US008034916B2

(12) United States Patent  
Dickey et al.

(10) Patent No.: US 8,034,916 B2  
(45) Date of Patent: Oct. 11, 2011

(54) **EXPRESSION CONTROL ELEMENTS FROM THE *LEMNACEAE* FAMILY**

(75) Inventors: Lynn F. Dickey, Cary, NC (US); Kevin M. Cox, Raleigh, NC (US); Charles G. Peele, Apex, NC (US)

(73) Assignee: Biolex Therapeutics, Inc., Pittsboro, NC (US)

( * ) Notice: Subject to any disclaimer, the term of this patent is extended or adjusted under 35 U.S.C. 154(b) by 0 days.

(21) Appl. No.: 12/581,752

(22) Filed: Oct. 19, 2009

(65) Prior Publication Data

US 2010/0043099 A1 Feb. 18, 2010

Related U.S. Application Data

(62) Division of application No. 11/653,593, filed on Jan. 16, 2007, now Pat. No. 7,622,573.

(60) Provisional application No. 60/759,308, filed on Jan. 17, 2006, provisional application No. 60/848,961, filed on Oct. 3, 2006.

(51) Int. Cl.
*C07H 21/04* (2006.01)
*A01H 5/00* (2006.01)
*C12N 15/05* (2006.01)
*C12N 15/82* (2006.01)

(52) U.S. Cl. ............. 536/24.1; 536/23.4; 536/23.6; 800/298; 800/295; 800/278; 800/288; 435/468; 435/419

(58) Field of Classification Search .............. None
See application file for complete search history.

(56) References Cited

U.S. PATENT DOCUMENTS

| | | | |
|---|---|---|---|
| 5,510,474 | A | 4/1996 | Quail et al. |
| 5,614,399 | A | 3/1997 | Quail et al. |
| 6,020,190 | A | 2/2000 | Quail et al. |
| 6,054,574 | A | 4/2000 | Quail et al. |
| 6,528,701 | B1 | 3/2003 | Wang et al. |
| 2003/0033630 | A1* | 2/2003 | Stomp et al. .......... 800/278 |
| 2007/0006347 | A1 | 1/2007 | Plesch et al. |
| 2007/0180583 | A1 | 8/2007 | Dickey et al. |

OTHER PUBLICATIONS

Maiti et al. Promoter/leader deletion anaylsis and plant expression vectors with the figwort mosaic virus (FMV) full length transcript (FLt) promoter containing single or double enhancer domains. (1997) Transgen. Res.; vol. 6; pp. 143-156.*
Doelling et al. The minimal ribosomal RNA gene promoter of *Arabidopsis thaliana* includes a critical element at the transcription initiation site. (1995) Plant J.; vol. 8; pp. 683-692.*
Donald et al. Mutation of either G box or I box sequences profoundly affects expression from the *Arabidopsis* rbcS-1A promoter. (1990) EMBO J. vol. 9; pp. 1717-1726.*
Benfey et al. The cauliflower mosaic virus 35S promoter: combinatorial regulation of transcription in plants. (1990) Science; vol. 250; pp. 959-966.*
Kim et al. A 20 nucleotide upstream element is essential for the nopaline synthase (nos) promoter activity. (1994) Plant Mol. Biol. vol. 24; pp. 105-117.*
Kehoe et al. Two 10-bp regions are critical for phytochrome regulation of a Lemna gibba Lhcb gene promoter. (1994) The Plant Cell; vol. 6; pp. 1123-1134.*
Gillikin et al. A defective signal peptide tethers the floury-2 zein to the endoplasmic reticulum membrane. (1997) Plant Physiol.; vol. 114, pp. 345-352.*
Stark et al. Two enhancers and one silencer located in the introns of a regA control somatic cell differentiation in Volvox carteri. (2001) Genes & Develop.; vol. 15; pp. 1449-1460.*
Williams, S.A., "NPR Genes, Which are Negatively Regulated by Phytochrome Action in Lemma gibba L. G-3, Can Also Be Positively Regulated by Abscisic Acid," *Plant Physiol.*, 1994, pp. 949-954, vol. 105.
Benfey, P.N., and N-H Chua, "The Cauliflower Mosaic Virus 35 S Promoter: Combinatorial Regulation of Transcription in Plants," *Science*, Nov. 16, 1990, pp. 959-966, vol. 250.
Chaubet-Gigot, Nicole, et al., "Tissue-Dependent Enhancement of Transgene Expression by Introns of Replacement Histone H3 Genes of *Arabidopsis*", Plant Molecular Biology, 2001, vol. 45, pp. 17-30.
Doelling, J.H., and C.S. Pikaard, "The Minimal Ribosomal RNA Gene Promoter of *Arabidopsis thaliana* Includes a Critical Element at the Transcription Initiation Site," *Plant J.*, 1995, pp. 683-692, vol. 8, No. 5.
Donald, R.G.K., and A.R. Cashmore, "Mutation of Either G Box or I Box Sequences Profoundly Affects Expression from the *Arabidopsis* rbcS-1A Promoter," *The EMBO Journal*, 1990, pp. 1717-1726, vol. 9, No. 6.
Hondred, David, et al., "Use of Ubiquitin Fusions to Augment Protein Expression in Transgenic Plants", *Plant Physiology*, Feb. 1999, vol. 119, pp. 713-723.
Kehoe, D.M., et al., "Two 10-bp Regions are Critical for Phytochrome Regulation of a *Lemna gibba Lhcb* Gene Promoter," *Plant Cell*, Aug. 1994, pp. 1123-1134, vol. 6, No. 8.

(Continued)

*Primary Examiner* — Cathy Kingdon Worley
(74) *Attorney, Agent, or Firm* — Alston & Bird LLP

(57) ABSTRACT

Compositions and methods for regulating expression of nucleotide sequences of interest in a plant are provided. Compositions include novel nucleic acid molecules, and variants and fragments thereof, for expression control elements isolated from the *Lemnaceae* ubiquitin, r-histone and chitinase genes. A method for expressing a nucleotide sequence of interest in a plant using the expression control elements disclosed herein is further provided. The method includes introducing into a plant or plant cell or nodule an expression construct comprising an expression control element of the present invention operably linked to a nucleotide sequence of interest. In particular, the compositions and methods find use in enhancing expression of nucleotide sequences of interest in duckweed. Also provided is a novel *Lemnaceae* signal peptide-encoding sequence and the signal peptide encoded thereby. Where an expression construct of the invention is designed to express a polypeptide of interest, this novel signal peptide-encoding sequence can be included within the expression construct of the invention to provide for extracellular secretion of the encoded polypeptide of interest.

23 Claims, No Drawings

OTHER PUBLICATIONS

Kim, Y., et al., "A 20 Nucleotide Upstream Element is Essential for the Nopaline Synthase (*nos*) Promoter Activity," *Plant Molecular Biology*, 1994, pp. 105-117, vol. 24.

Maiti, I.B., et al., "Promoter/Leader Deletion Analysis and Plant Expression vectors with the Figwort Mosaic Virus (FMV) Full Length Transcript (FLt) Promoter Containing single or Double Enhancer Domains," *Transgenic Research*, 1997, pp. 143-156, vol. 6.

Ngsee, J.K., et al., "Cassette Mutagenic Analysis of the Yeast Invertase Signal Peptide: Effects on Protein Translocation," *Molecular and Cellular Biology*, Aug. 1989, pp. 3400-3410, vol. 9, No. 8.

Plesse, B., et al., "Effects of the Polyubiquitin Gene *Ubi.U4* Leader Intron and First Ubiquitin Monomer on Reporter Gene Expression in *Nicotiana tabacum*", *Plant Molecular Biology*, 2001, vol. 45, pp. 655-667.

Rolfe, S.A., and E.M. Tobin, "Deletion Analysis of a Phytochrome-regulated Monocot rbcS Promoter in a Transient AssaySystem," *Proc. Natl. Acad. Sci.*, Apr. 1991, pp. 2683-2686, vol. 88, No. 7.

Sivamani, Elumalai, et al., "Expression Enhancement of a Rice Polyubiquitin Gene Promoter", *Plant Molecular Biology*, 2006, vol. 60, pp. 225-239.

Sun, Chih-Wen, et al., "Independent Modulation of *Arabidopsis thaliana* Polyubiquitin mRNAs in Different Organs and in Response to Environmental Changes", *The Plant Journal*, 1997, vol. 11(5), pp. 1017-1027.

Wang, J., et al., "Rice Ubiquitin Promoters: Deletion Analysis and Potential Usefulness in Plant Transformation Systems", 2003, *Plant Cell Reports*, pp. 1-16.

Wang, Jianlin, et al., Structure, Expression and Promoter Activity of Two Polyubiquitin Genes from Rice (*Oryza sativa L.*), *Plant Science*, 2000, vol. 156, pp. 201-211.

Waterborg, Jakob, H., et al., "Common Features of Analogous Replacement Histone H3 Genes in Animals and Plants", *J. Mol. Evol.*, 1996, vol. 43, pp. 194-206.

Wei, Hairong, et al., "Comparative Expression Analysis of Two Sugarcane Polyubiquitin Promoters and Flanking Sequences in Transgenic Plants", *J. Plant Physiol.*, 2003, vol. 160, pp. 1241-1251.

EMBL Database Accession No. AL161589, submitted on Mar. 10, 2000 (XP002459417).

* cited by examiner

SEQUENCE LISTING

<160> NUMBER OF SEQ ID NOS: 16

<210> SEQ ID NO 1
<211> LENGTH: 2160
<212> TYPE: DNA
<213> ORGANISM: Lemna minor

<400> SEQUENCE: 1

```
agtcgagtga tatgaaatct tggtgaagaa ggatcggaga acggaccggg tgaggcaagg      60
ataattctgc tgttaaattc gagagcaaga cacctgcaat tcaagaatcg agtggcaatt     120
aatatagcag gatgatctgg aaggtagatc ctgcccatcg aatgatccaa acatcaacac     180
taggatcata ccgttaacaa taatgaatga aaaagtagaa gatgacgaag ttgaagtgat     240
gaccaaaaac tttgaaaatt ccaaccgtat ggccggaatc agtgtgaaga aaatcgaaat     300
caaatactct aatggatcgg attgttattc tggaggcaaa tctgaaactt cgaggatagg     360
atttaatcca cgcaagtaat aatttgaaac tcagaaggag aaaaaaaaac taaaatagag     420
aagaagagat ctcaaagaag ccgtgagcac gagacgaacg agaagaggta agcaccagt     480
cagaggaaaa caccaaaatt agagaaatag cacgaacatt aaagcacaga tccgcgccgc     540
aaacccgaaa gacgaaaaat agagccaaac gaaaccctaa taatcgatct gcacaaaaaa     600
aaaaaaaaaa aactttgaga agagccgcga aattacccta gaatcctcag aactggccgg     660
acgagagaag cgctcgatcg aaacccaaca taaaacccct tccaacggca aattactccg     720
caaaacccga aaaataaaca aaatcaacga tcacgagaag gtgcaagggc aaaaagaggc     780
agtgcgatcg agagtctacc tgaatcgtcg gcgcaaaagg cgagcccacc gacgaacgct     840
ccctctagaa cctggagatg cggcgagaga gaaggaaaga tcttcggtgg gtgatgctcg     900
ctatttatcg caagagagtt agagagatct tcttcggcgg cggatttctg gcatctagcg     960
tttaacctca ccgcccagtg ctcacatcct tcttctcata tttgaatatt taattaacaa    1020
atgaatcagt cattttttctt taatttttaa ttcccggaga gggcaatgtt ggtatcaaaa    1080
attatttagg aaaaattaat tacacgaata atcggatttt tcccttttt taattaattt    1140
ctaattttgg aaaaggaaag aaaaatttta ggggtatgga gggcaagaat gaaatattac    1200
aaaattaggg gttttgcgt aatttattat atttaataaa gaaagtcgaa tattcccatc    1260
cgattggtag ttgaaagggg ccgaaaggcc tcggggtttc tagagatttc tacattattc    1320
tcgttttttgt cgccaagaag gtgggcaatt atgtttcatg ccttaacttc ttcttttttgt    1380
gggaatactc ttattcttag tacaaaagaa aagagtatat gcataaataa gatgaaaaat    1440
gggtttattc gagatttcta cgtcatgtgt gactcgctta ggaaatatcg ccgaaaccta    1500
acaaaggcgg tacgctcctc tcccccgacc tataaataga gacctttgcc tcgtctttct    1560
caactcaagc atttctgtat gatccttctc tttccgcgga agctctcgcg ccagttgatc    1620
gcaaggtatg cgtctttcct ccttgtgatt cgatctttct gttggctaga tctggtctat    1680
tgatctgctc tattgatctg gtctatttat cgctgcatcg ggatctattg atccgtatgt    1740
tgatttggga tccgtaggtt ggtttggatc ggagactgcg atttgattct tgtgatttcg    1800
cttggatttc ggaaatcggt gtggttgaag tcgtgcgatc ttttagatct gctccttttt    1860
ttatttgcta ttttatattt acgttgttta tgatcgcgga ttattttgat tcgtttattc    1920
gagatccatg ccgtttaact cgttctttgt gctccgatct ttgcgatacg tcggtcgttc    1980
tagatccgtt cactaggtta gttttaagtt ctttgagctt gatttatatg gatttgctgt    2040
```

-continued

| | |
|---|---|
| tttccaggaa aaatttatgc gcgattctta cgcccgtttc cccatttttac tttaggtcgt | 2100 |
| gaattctttt gatctgagaa tgatgaatct gacatgtacc ttccggtttg taatttgcag | 2160 |

<210> SEQ ID NO 2
<211> LENGTH: 2021
<212> TYPE: DNA
<213> ORGANISM: Spirodela polyrrhiza

<400> SEQUENCE: 2

| | |
|---|---|
| caaataaaga gatggacaga taatgagatg aattagaaaa aaaaaattcg tgttgtaaga | 60 |
| tagaatactt gctatctact gatgaatgca gttcagtttt cctcacgatc ttaaagatcg | 120 |
| cgcactatcc tcagcttcac tctggaaatt ttgattctct tcttctgctc agcagcctcg | 180 |
| actctgtcta gggtttcgta caatcggacg ccattctaca tgaatcgagc acagggaatg | 240 |
| aagacaatta ggagatcctc gatgtcctcc gacttacttg catgacttga cggggaagat | 300 |
| ctcgagcagg gaagcgacgc ctctccggag gactcgcctc gccgagagga cctcctccgc | 360 |
| gacacggacc atggcctcca cggggtagaa gctggccctg ttctttattc tcttgaggat | 420 |
| catcggccga agcctccgca aatccatccc gaggagtag aatctcgcct gcaggaagca | 480 |
| tctgtcgaga tcctcgccga ggcggcggag atacctcgcc ggcgccgcca tggcgccggg | 540 |
| gacggagcac caccacggag aagaagaacc ctaacccaag gcattaacga agttgcgcag | 600 |
| attatacaaa agccctcaaa tatctttcat tttctatttc actgatacat tttcattatt | 660 |
| gtatatgagt gttatttaa attattccgt attagaaaag cacctccaga acccgacaaa | 720 |
| atagggtgac gtcatcatgg tgtcatgacc gcccaacagc cgcagattta aaatcggtgg | 780 |
| atgagtgcgg ccacgccacg aaagcgatgg gccttcgtcg atgccgtgag aatccatctg | 840 |
| acataaagta aacggcgccg tcagtattga cggcgtatga cacgtggaaa gaagctattg | 900 |
| gttcacgcat cggtggttcc gctagcctcc gtcgaccgct agtactataa atacggtccc | 960 |
| gaggcctcct caccactcgc acatatcctc tttgttttcc tctccgtgaa agaagcgagg | 1020 |
| aagcgcgtcg tctctcccaa ggtaaggagc agatctcttt gatcgttttt gttcttcttt | 1080 |
| tgttttgttt ttttttttctg cggatcttcg gttgcatcat gccttggctg tttttattag | 1140 |
| tttaggatat cctcgtttgg atctgagccg atcatatatg ttaaaggttg tgttcgatct | 1200 |
| ctttgttcat tttcgcatga aaaggatgta tccttttgat gtgaggcgat cttctatggt | 1260 |
| taagactttg ttcggtctat tgatcatttc tgttcttcgt ttttgagttt ttttctgcgg | 1320 |
| atatcgcatc atccctaggt ttttgctttg gttaggatgc atcctttgga tttgagccga | 1380 |
| tctcccttgg ttaaggctgt gtctgttgca gaggagaaag tctgtcgagg tccttatgca | 1440 |
| ggctttgtcc agatgcgcgt gctctctcat gctatgaatt tatgtttga gaactcctcc | 1500 |
| cggtttttct agatccggat ttgaagtatt cattgcggtt ccccttcggt tttatgtatt | 1560 |
| tctcgagttg atttggtcca tgatcgtgtt ctgtccagat ctctcttgat atggatgaga | 1620 |
| tattcgttac ctcttttcaaa catcggtgga tgttcttttt agtcttggct caccttatc | 1680 |
| tagaaattaa ttttcggttt gaaacccctg cttgttaagg tgatgtattc cttcttata | 1740 |
| gatttcggtg tgttatttct taacggtgat ctgtccgatc catgtgttgc acctcttgtt | 1800 |
| ttctgtgtaa tcctctgtga attataatta tgttttgaaa acgtacttaa gtaaggggca | 1860 |
| tgttccccgt ttaaaacttt tgttctatca atttgtggtt aatagatcct gatttgtggt | 1920 |
| cgccttattc tgtctttaat cgtggatttt atttatcttg agcgcgtcct tttcttttaa | 1980 |
| aatcatgtgt ttaacctttc agtcgtcata tgttccatca g | 2021 |

<210> SEQ ID NO 3
<211> LENGTH: 2068
<212> TYPE: DNA
<213> ORGANISM: Lemna aequinoctialis

<400> SEQUENCE: 3

| | | | | | |
|---|---|---|---|---|---|
| agtgtaccaa | tattttaaac | cctacattta | tcattcttta | ttcattattg | ccataagtta | 60 |
| atgaatattg | aaattcaaat | acgcgcaaga | tgtcaatatc | gatcgaatat | gaataccaga | 120 |
| tataaaatca | aaatcaaat | atcaaattaa | taaagatata | aaatattgaa | tccaaaagca | 180 |
| ataaagaata | tcactattaa | tatcaaaata | tcgatttgaa | gttcaaaaat | tgggtccatt | 240 |
| aggagccaag | accgatcatg | atccgatact | gatatcaata | tctgtagctc | agtggctagg | 300 |
| cccctcaatt | tgcctggccg | aaggcagtgt | acaaaacctg | gctctcgcaa | gggcaaagaa | 360 |
| agagtctttc | ccaaaaaaaa | aaaaatcgaa | cccatttgta | gtatccaata | tttggattga | 420 |
| cataagatac | caaaacataa | agtactaacc | acccaatctt | ataattaatc | aagatttata | 480 |
| tcacatccaa | tatcaagatc | cgatatcaat | acctagaccg | gtaaacccta | atttactctt | 540 |
| cccccctcta | aaaatttcca | ataaatatct | ccacatattt | aactattaaa | aaattgataa | 600 |
| gagataggcc | ctagccctaa | gtcctaacat | ataaccactc | tctatgaaaa | gtcctattaa | 660 |
| atgacgtcat | ttatttattt | attgccggtt | ggctgctcca | cagccgcaat | taatggatg | 720 |
| gctgacacgg | cacgaaaccg | acgggcggtg | ccgtgggaat | aattctagag | taaacctaac | 780 |
| ggcgccgtta | actttgacgg | tggcgaagac | gcgtggggat | aggtggttgg | tccgcgtgac | 840 |
| ggcggcggtt | cagcccgtcg | accttgagcc | gagactataa | atcgaggcga | agggatgagc | 900 |
| tttgccattg | cgttcttctt | ctgttcatct | ctgaaattcg | ggcggaatcc | ttcttcttct | 960 |
| caaggtatgg | gcctcgatct | ttctgtttca | atcgagtttt | gatcttcgtt | ttggcggcga | 1020 |
| tcggtgtttt | ctttgtattg | tgaataaatc | cttgataaga | aaaccctagg | ttttgtgacc | 1080 |
| tgttgacgga | tgcgtgcgga | tctgttattt | gtcttttagg | cgattttctc | ttgtttgtaa | 1140 |
| tagtttatca | taaccagatg | aacatggatc | aagtcgattt | gacttatttt | ttctgtgaaa | 1200 |
| ttaggccgaa | atccttttttt | ttggtttgag | ccttgatatt | tctatataat | tcgatttgat | 1260 |
| tttttgtttt | cttctgcgtc | tgatgctttc | tcttgactcc | tgattaaatt | tttgctacgg | 1320 |
| aaaccctaga | tgtcgagatc | tgttgacaga | ttctggcaaa | tctgttttta | tcataatcag | 1380 |
| atgaacgcaa | attaagtcga | tttggttttt | ctctgaaatt | agggggaaa | ctccttatag | 1440 |
| tatgagcctc | gatatttcta | taatagtcga | tttgattttc | tcttgcctcc | tgattcaatt | 1500 |
| tttggtgcgg | aaaccctaga | tattgtaatc | tgtttacgga | tgcttgcgga | tctgattttt | 1560 |
| aatattgtga | tctattgacg | gatgctcgta | gatctggttg | ttttgatttc | ttcatgcctt | 1620 |
| atacggcgat | ttgattcggc | gattaaaaat | tttcaattct | tttaaaaaaa | atattaagat | 1680 |
| tttcaacgtt | tcaaattatt | tcatagatcg | gcacaaatac | ttttcatcag | attcctcctg | 1740 |
| atgtgatggt | ttgtgtttaa | aatctgttga | agatatcaga | ttctattagg | tcaccgatat | 1800 |
| aatcttctct | gttattctg | cgatcggtgc | ttacaaaccc | tatttcctac | ggtgattaat | 1860 |
| tatttttaat | ctcctagcta | gcgtaaatat | atattttttt | aatttgatct | ttgcattagt | 1920 |
| ttcctccttt | tatttgctat | taattgtaac | cgatgctaca | aaacatcaga | ttttttttcc | 1980 |
| caattcgttg | tcatcattat | agaaaacttt | tatctgatat | ttttaatcgt | cattaatata | 2040 |
| attttcaatt | tattatttc | ccttgcag | | | | 2068 |

<210> SEQ ID NO 4

```
<211> LENGTH: 1625
<212> TYPE: DNA
<213> ORGANISM: Lemna minor

<400> SEQUENCE: 4
agtcgagtga tatgaaatct tggtgaagaa ggatcggaga acggaccggg tgaggcaagg      60
ataattctgc tgttaaattc gagagcaaga cacctgcaat tcaagaatcg agtggcaatt     120
aatatagcag gatgatctgg aaggtagatc ctgcccatcg aatgatccaa acatcaacac     180
taggatcata ccgttaacaa taatgaatga aaaagtagaa gatgacgaag ttgaagtgat     240
gaccaaaaac tttgaaaatt ccaaccgtat ggccggaatc agtgtgaaga aaatcgaaat     300
caaatactct aatggatcgg attgttattc tggaggcaaa tctgaaactt cgaggatagg     360
atttaatcca cgcaagtaat aatttgaaac tcagaaggag aaaaaaaaac taaaatagag     420
aagaagagat ctcaaagaag ccgtgagcac gagacgaacg agaagaggta aagcaccagt     480
cagaggaaaa caccaaaatt agagaaatag cacgaacatt aaagcacaga tccgcgccgc     540
aaacccgaaa gacgaaaaat agagccaaac gaaaccctaa taatcgatct gcacaaaaaa     600
aaaaaaaaaa aactttgaga agagccgcga aattacccta gaatcctcag aactggccgg     660
acgagagaag cgctcgatcg aaacccaaca taaaacccct tccaacggca aattactccg     720 caaacccga aaataaaca aaatcaacga tcacgagaag gtgcaagggc aaaaagaggc     780
agtgcgatcg agagtctacc tgaatcgtcg gcgcaaaagg cgagcccacc gacgaacgct     840
ccctctagaa cctggagatg cggcgagaga aaggaaaga tcttcggtgg gtgatgctcg     900
ctatttatcg caagagagtt agagagatct tcttcggcgg cggatttctg gcatctagcg     960
tttaacctca ccgcccagtg ctcacatcct tcttctcata tttgaatatt taattaacaa    1020
atgaatcagt cattttcctt taattttta ttcccggaga gggcaatgtt ggtatcaaaa    1080
attatttagg aaaaattaat tacacgaata atcggatttt tcccttttt taattaattt    1140 ctaattttgg aaaaggaaag aaaaatttta ggggtatgga gggcaagaat gaaatattac    1200
aaaattaggg gttttgcgt aatttattat atttaataaa gaaagtcgaa tattcccatc    1260
cgattggtag ttgaaagggg ccgaaaggcc tcggggtttc tagagatttc tacattattc    1320 tcgttttgt cgccaagaag gtgggcaatt atgtttcatg ccttaacttc ttcttttgt    1380 gggaatactc ttattcttag tacaaaagaa aagagtatat gcataaataa gatgaaaaat    1440
gggtttattc gagatttcta cgtcatgtgt gactcgctta ggaaatatcg ccgaaaccta    1500
acaaaggcgg tacgctcctc tcccccgacc tataaataga gacctttgcc tcgtctttct    1560
caactcaagc atttctgtat gatccttctc tttccgcgga agctctcgcg ccagttgatc    1620
gcaag                                                                1625

<210> SEQ ID NO 5
<211> LENGTH: 1041
<212> TYPE: DNA
<213> ORGANISM: Spirodela polyrrhiza

<400> SEQUENCE: 5
caaataaaga gatggacaga taatgagatg aattagaaaa aaaaaattcg tgttgtaaga      60
tagaatactt gctatctact gatgaatgca gttcagtttt cctcacgatc ttaaagatcg     120
cgcactatcc tcagcttcac tctggaaatt ttgattctct tcttctgctc agcagcctcg     180
actctgtcta gggtttcgta caatcggacg ccattctaca tgaatcgagc acagggaatg     240
aagacaatta ggagatcctc gatgtcctcc gacttacttg catgacttga cggggaagat     300
```

```
ctcgagcagg gaagcgacgc ctctccggag gactcgcctc gccgagagga cctcctccgc    360
gacacggacc atggcctcca cggggtagaa gctggccctg ttctttattc tcttgaggat    420
catcggccga agcctccgca aatccatccc cgaggagtag aatctcgcct gcaggaagca    480
tctgtcgaga tcctcgccga ggcggcggag ataccctcgcc ggcgccgcca tggcgccggg    540
gacggagcac caccacggag aagaagaacc ctaacccaag gcattaacga agttgcgcag    600
attatacaaa agccctcaaa tatctttcat tttctatttc actgatacat tttcattatt    660
gtatatgagt gtttatttaa attattccgt attagaaaag cacctccaga acccgacaaa    720 ataggtgac gtcatcatgg tgtcatgacc gcccaacagc cgcagattta aaatcggtgg    780
atgagtgcgg ccacgccacg aaagcgatgg gccttcgtcg atgccgtgag aatccatctg    840
acataaagta aacggcgccg tcagtattga cggcgtatga cacgtggaaa gaagctattg    900
gttcacgcat cggtggttcc gctagcctcc gtcgaccgct agtactataa atacggtccc    960
gaggcctcct caccactcgc acatatcctc tttgttttcc tctccgtgaa agaagcgagg   1020
aagcgcgtcg tctctcccaa g                                             1041

<210> SEQ ID NO 6
<211> LENGTH: 964
<212> TYPE: DNA
<213> ORGANISM: Lemna aequinoctialis

<400> SEQUENCE: 6
agtgtaccaa tattttaaac cctacattta tcattcttta ttcattattg ccataagtta     60
atgaatattg aaattcaaat acgcgcaaga tgtcaatatc gatcgaatat gaataccaga    120
tataaaatca aaaatcaaat atcaaattaa taaagtatata aaatattgaa tccaaaagca    180 ataagaata tcactattaa tatcaaaata tcgatttgaa gttcaaaaat tgggtccatt    240
aggagccaag accgatcatg atccgatact gatatcaata tctgtagctc agtggctagg    300
cccctcaatt tgcctggccg aaggcagtgt acaaaacctg gctctcgcaa gggcaaagaa    360
agagtctttc ccaaaaaaaa aaaaatcgaa cccatttgta gtatccaata tttggattga    420
cataagatac caaaacataa agtactaacc acccaatctt ataattaatc aagatttata    480
tcacatccaa tatcaagatc cgatatcaat acctagaccg gtaaacccta atttactctt    540 ccccccctcta aaaatttcca ataaatatct ccacatattt aactattaaa aaattgataa    600
gagataggcc ctagccctaa gtcctaacat ataaccactc tctatgaaaa gtcctattaa    660
atgacgtcat ttatttattt attgccggtt ggctgctcca cagccgcaat ttaatggatg    720
gctgacacgg cacgaaaccg acgggcggtg ccgtgggaat aattctagag taaacctaac    780
ggcgccgtta actttgacgg tggcgaagac gcgtggggat aggtggttgg tccgcgtgac    840
ggcggcggtt cagcccgtcg accttgagcc gagactataa atcgaggcga agggatgagc    900
tttgccattg cgttcttctt ctgttcatct ctgaaattcg ggcggaatcc ttcttcttct    960
caag                                                                 964

<210> SEQ ID NO 7
<211> LENGTH: 535
<212> TYPE: DNA
<213> ORGANISM: Lemna minor

<400> SEQUENCE: 7
gtatgcgtct ttcctccttg tgattcgatc tttctgttgg ctagatctgg tctattgatc     60
tgctctattg atctggtcta tttatcgctg catcgggatc tattgatccg tatgttgatt    120
```

```
tgggatccgt aggttggttt ggatcggaga ctgcgatttg attcttgtga tttcgcttgg      180
atttcggaaa tcggtgtggt tgaagtcgtg cgatctttta gatctgctcc tttttttatt      240
tgctatttta tatttacgtt gtttatgatc gcggattatt ttgattcgtt tattcgagat      300
ccatgccgtt taactcgttc tttgtgctcc gatctttgcg atacgtcggt cgttctagat      360
ccgttcacta ggttagtttt aagttctttg agcttgattt atatggattt gctgttttcc      420
aggaaaaatt tatgcgcgat tcttacgccc gtttccccat tttactttag gtcgtgaatt      480
cttttgatct gagaatgatg aatctgacat gtaccttccg gtttgtaatt tgcag          535

<210> SEQ ID NO 8
<211> LENGTH: 980
<212> TYPE: DNA
<213> ORGANISM: Spirodela polyrrhiza

<400> SEQUENCE: 8
gtaaggagca gatctctttg atcgttttg ttcttctttt gttttgtttt ttttttctgc       60
ggatcttcgg ttgcatcatg ccttggctgt ttttattagt ttaggatatc ctcgtttgga      120
tctgagccga tcatatatgt taaaggttgt gttcgatctc tttgttcatt ttcgcatgaa      180
aaggatgtat cctttgatg tgaggcgatc ttctatggtt aagactttgt tcggtctatt      240
gatcatttct gttcttcgtt tttgagtttt tttctgcgga tatcgcatca tccctaggtt      300
tttgctttgg ttaggatgca tcctttggat ttgagccgat ctcccttggt taaggctgtg      360
tctgttgcag aggagaaagt ctgtcgaggt ccttatgcag gctttgtcca gatgcgcgtg      420
ctctctcatg ctatgaattt atgttttgag aactcctccc ggttttttcta gatccggatt      480 tgaagtattc attgcggttc cccttcggtt ttatgtattt ctcgagttga tttggtccat      540
gatcgtgttc tgtccagatc tctcttgata tggatgagat attcgttacc tctttcaaac      600
atcggtggat gttcttttta gtcttggctc acctttatct agaaattaat tttcggtttg      660
aaacccctgc ttgttaaggt gatgtattcc ttctttatag atttcggtgt gttatttctt      720
aacggtgatc tgtccgatcc atgtgttgca cctcttgttt tctgtgtaat cctctgtgaa      780
ttataattat gttttgaaaa cgtacttaag taaggggcat gttccccgtt taaaactttt      840
gttctatcaa tttgtggtta atagatcctg atttgtggtc gccttattct gtctttaatc      900
gtggatttta tttatcttga gcgcgtcctt ttccttttaaa atcatgtgtt taaccttca      960 gtcgtcatat gttccatcag                                                 980

<210> SEQ ID NO 9
<211> LENGTH: 1104
<212> TYPE: DNA
<213> ORGANISM: Lemna aequinoctialis

<400> SEQUENCE: 9
gtatgggcct cgatctttct gtttcaatcg agttttgatc ttcgttttgg cggcgatcgg       60
tgttttcttt gtattgtgaa taaatccttg ataagaaaac cctaggtttt gtgacctgtt      120
gacggatgcg tgcggatctg ttatttgtct tttaggcgat tttctcttgt ttgtaatagt      180
ttatcataac cagatgaaca tggatcaagt cgatttgact tattttttct gtgaaattag      240
gccgaaatcc ttttttttgg tttgagcctt gatatttcta tataattcga tttgattttt      300
tgttttcttc tgcgtctgat gctttctctt gactcctgat taaattttg ctacggaaac       360 cctagatgtc gagatctgtt gacagattct ggcaaatctg tttttatcat aatcagatga      420
acgcaaatta agtcgatttg gttttctct gaaattaggg gggaaactcc ttatagtatg       480
```

```
agcctcgata tttctataat agtcgatttg attttctctt gcctcctgat tcaattttg     540 gtgcggaaac cctagatatt gtaatctgtt tacggatgct tgcggatctg attttaata    600 ttgtgatcta ttgacggatg ctcgtagatc tggttgtttt gatttcttca tgccttatac   660
ggcgatttga ttcggcgatt aaaaattttc aattcttta aaaaaaatat taagattttc    720
aacgtttcaa attatttcat agatcggcac aaatactttt catcagattc ctcctgatgt   780
gatggtttgt gtttaaaatc tgttgaagat atcagattct attaggtcac cgatataatc   840
ttctctgttt attctgcgat cggtgcttac aaacccctatt tcctacggtg attaattatt  900
tttaatctcc tagctagcgt aaatatatat ttttttaatt tgatctttgc attagtttcc   960
tccttttatt tgctattaat tgtaaccgat gctacaaaac atcagatttt ttttcccaat  1020
tcgttgtcat cattatagaa aactttatc tgatatttt aatcgtcatt aatataattt   1080
tcaatttatt attttcccett gcag                                         1104

<210> SEQ ID NO 10
<211> LENGTH: 64
<212> TYPE: DNA
<213> ORGANISM: Lemna gibba

<400> SEQUENCE: 10
aagcacgagc tgagcgagaa ttcggggagg ctgagtcgaa gaggaagaga gaagtaggta    60
cgcc                                                                64

<210> SEQ ID NO 11
<211> LENGTH: 58
<212> TYPE: DNA
<213> ORGANISM: Lemna gibba

<400> SEQUENCE: 11
actcgcaagt ggagagagga tccgagcgtc cagtgagagg aagagagagg gaggcgcg      58

<210> SEQ ID NO 12
<211> LENGTH: 62
<212> TYPE: DNA
<213> ORGANISM: Lemna gibba

<400> SEQUENCE: 12
aaactcccga ggtgagcaag gatccggagt cgagcgcgaa gaagagaaag agggaaagcg    60
cg                                                                  62

<210> SEQ ID NO 13
<211> LENGTH: 1808
<212> TYPE: DNA
<213> ORGANISM: Lemna minor
<220> FEATURE:
<221> NAME/KEY: misc_feature
<222> LOCATION: (598)..(598)
<223> OTHER INFORMATION: n is a, c, g or t

<400> SEQUENCE: 13
agattgttgt gagagagcga cagcacctgg agcgccggaa gctcgccgat cgccggagga    60
actatgcctt gaagcgcatt cccgtgcaag ctaatgtgca gaatggagct gcagttcgtg   120
agagcggctg gaagagtccc ttcgagaaga ttccagtcca gccagaggta agaagatcc    180 tgaagcccgc caatgtcgac cgggatcgtc cctgtgaggc gattgaacga gagattgatg   240
aactggagac gaggagaggc ggagagactg cctggaatct cgccggagaa gccattggag   300
gagggatcga ggtaccgaag ccccgccgga agagcgggag ggattccgcc ggagaaattg   360
```

```
ttgccagcga ggtttaggac ctgagggatg caagattgga agggaaatct ggcggaaggt    420
cgccggagag gcggttgttc tgcaagaaga gggatcggag ttggcggaga gaggagaatg    480
cggccggaat gctgccattg aacgcgttgc cgcggagact gagccggcgg agttgagaaa    540
gatcggcgag gcgcccggag atcggaccag agagatggag aagagggagg cggagctnca    600
cgacgcggga atcgccggag gtggaacaga gaacgccgcg ccatgagcac ggagcggaaa    660
gcattgaggc gttccagtca gagagagccc cgtgcggatc gtaaagggag aagcggaact    720
tctccagcgc tctgatctcc gccagggatt ccggagggat cttctgctcc tgccccgcgg    780
tggaaatgag gaagagaatg aagagaagga agtggaggag agaggacgcc atggtagcag    840
aggaaggtct ggcttgatct cccgacgatt cctctctcat cagtgaaaca agagaataag    900
aggcatcgcg attcttggaa ggtacagagg gaagttgatc aaagagaggc tccgggaaga    960
agcagatggc ggggaagacg aaacatggcg cctgacaaca taggctatca taggataatc   1020
cactctccct ctgtctttct ctctgtttct ttctctctct ctttatctct ctctctctct   1080
cgaacatttc acacattttt gggcctgttc tttggcgtag ctagccctt cttggtccat    1140
attttgaggc caaggccaat catgcgcagc cacgttgcat ggcgggagga ccccatctat   1200
ccattccgtc agttcctggc ttttgggaca atctgaacag tacataaacc acgggctcgg   1260
gcttgggccc gccgaaaagc ccgtccgtac aattttctga cgtacaatat taatttccca   1320
gaaaagaaaa ttcattaaaa aataactatg tcacccacga actcgtgatc tagatataag   1380
gcaggcaact ttcccgtgac agtcggactt gtggggttcc cttgacgcg ccgccgtcta    1440
ctgacggcgc ttgaatgacg tcattattac tatatttaat atatccgaga ataaatggct   1500
ccctggatcc cccgtgaatg gtcacgtcat ccacgcgggc tttgacttcg cctaggtcgc   1560
cacgttgggg cctcataacg tgcaagctga cgtggctatc attgcctcga tggcgatctt   1620
gaacgaacca cataaccaat ctgagacggc gacgaggatt ctgtgttttc ctcgggatc    1680
tctggccgtc cgatgaacta acacgcacta tttcaaaaag ggggttaaac acgattgtta   1740
ggtttctttg agtcttccac atctccgctc cacgatcttg tacctcttct tgcgacgatc   1800
tactcgcc                                                            1808

<210> SEQ ID NO 14
<211> LENGTH: 1338
<212> TYPE: DNA
<213> ORGANISM: Lemna minor

<400> SEQUENCE: 14
ttcgagtttg gtgttcttga atattttttc ccattttttt tttctatttt tgagcttttc     60
tccgtctttg cggggatctt gtgtcggaga ggtggcccgt gccactggcg gtctacgggc    120
ggtttctctg gtaggttagg ctgttggacg tcgtcatctc ccccaaaggc agcaggcggc    180
ggcgctccag cgtaaggcct aacgccgcgt ctgctcgaga tcgcctagcg tgatcagggc    240
tcgggaacc tcccgagggg gagcacgatt tctctccatt cctctcttct tgatgtcttt    300
ggcggcttcg gtatgggaag ggatcaactg gtagcagcga agcagatggt ccaccatcat    360
gaagtcaatt aatacattta aaatgagatg ttgatgggga attaaaataa gtaaaacaaa    420
atattgcaag tgctcatgtt tcaaacctcc ttgtcttagt tcttaagttc acatcacttg    480
aggtttcaca cctccatgcc ctagttcttg ccttggttct tgaattcaca ccacttaagg    540
gaatatttaa atatttaaaa tttatgttta actgattaag aagattgaac ctgtcgagga    600
gacgacattt agtttcttct actaggaaaa aaaattattc gagagaaagg gccaaagttt    660
```

```
cacacctcca taccctactt ctttaattca caccactcaa gggaatattt agatatttaa    720
attttatatt taactgatta agaagattgc acctaacgag gagacgatat ttagtttctt    780
ccactagaaa aaaaataaaa atactaaatt attcgagagg aaggcccgaa tgttgcagcc    840
gccagtaaat attatccagg aaaaaaaatt atcctatcca cgacaaaacc ttcttcacaa    900
aatacgataa tcagaataat gaatatgatg ttttgaaaat tcccgatagg gtttggcgag    960
atggcgtcgt cagctaggga agaggtgaca gcgataggcg ctgaaaaact gccgcagcag   1020
acagagagcg ataaatgctg cacgcgcttt ctcttcactt gggtcagtgg gcgagttcga   1080
aggagacttg agtctcccct gggccagctc gttgaacgtt tctacgcggg taatccatcc   1140
ttcggcgaac gcgagacccc gtctggtcct ccgccgagtc ttcgatctgc tggaaaatgg   1200
caataatttc tctgatctcc ccgtctttgg caccacgatg gcgtgtagac tggggtcttc   1260
ttccacggac actaaataag taggaggcag cgaatggagt gtgaatcggc tcccccttcc   1320
gtcttcctct ttgaagtc                                                 1338
```

```
<210> SEQ ID NO 15
<211> LENGTH: 84
<212> TYPE: DNA
<213> ORGANISM: Lemna minor
<220> FEATURE:
<221> NAME/KEY: CDS
<222> LOCATION: (1)..(84)

<400> SEQUENCE: 15 atg gct gct ttg aac aat gct cgt ctt atc gcg ctc ttc ttc agc ttg        48
Met Ala Ala Leu Asn Asn Ala Arg Leu Ile Ala Leu Phe Phe Ser Leu
1               5                   10                  15 ggg ttc gta ctc tcc ctg cct tgg cct gcc cac gga                       84
Gly Phe Val Leu Ser Leu Pro Trp Pro Ala His Gly
            20                  25

<210> SEQ ID NO 16
<211> LENGTH: 28
<212> TYPE: PRT
<213> ORGANISM: Lemna minor

<400> SEQUENCE: 16

Met Ala Ala Leu Asn Asn Ala Arg Leu Ile Ala Leu Phe Phe Ser Leu
1               5                   10                  15

Gly Phe Val Leu Ser Leu Pro Trp Pro Ala His Gly
            20                  25
```

EXPRESSION CONTROL ELEMENTS FROM THE *LEMNACEAE* FAMILY

CROSS-REFERENCE TO RELATED APPLICATIONS

This application is a divisional patent application of U.S. patent application Ser. No. 11/653,593, filed Jan. 16, 2007, now U.S. Pat. No. 7,622,573, which claims the benefit of U.S. Provisional Patent Application Nos. 60/759,308, filed Jan. 17, 2006, and 60/848,961, filed Oct. 3, 2006, each of which is hereby incorporated in its entirety by reference herein.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 380989SequenceListing.txt, a creation date of Oct. 19, 2009, and a size of 26.7 KB. The sequence listing filed via EFS-Web is part of the specification and is hereby incorporated in its entirety by reference herein.

FIELD OF THE INVENTION

The present invention relates to compositions and methods for enhancing gene expression in plants.

BACKGROUND OF THE INVENTION

The duckweeds are the sole members of the monocotyledonous family *Lemnaceae*. The five genera and 38 species are all small, free-floating, fresh-water plants whose geographical range spans the entire globe (Landolt (1986) *Biosystematic Investigation on the Family of Duckweeds: The Family of Lemnaceae—A Monograph Study* (Geobatanischen Institut ETH, Stiftung Rubel, Zurich)). Although the most morphologically reduced plants known, most duckweed species have all the tissues and organs of much larger plants, including roots, stems, flowers, seeds and fronds. Duckweed species have been studied extensively and a substantial literature exists detailing their ecology, systematics, life-cycle, metabolism, disease and pest susceptibility, their reproductive biology, genetic structure, and cell biology (Hillman (1961) *Bot. Review* 27:221; Landolt (1986) *Biosystematic Investigation on the Family of Duckweeds: The Family of Lemnaceae—A Monograph Study* (Geobatanischen Institut ETH, Stiftung Rubel, Zurich)).

The growth habit of the duckweeds is ideal for microbial culturing methods. The plant rapidly proliferates through vegetative budding of new fronds, in a macroscopic manner analogous to asexual propagation in yeast. This proliferation occurs by vegetative budding from meristematic cells. The meristematic region is small and is found on the ventral surface of the frond. Meristematic cells lie in two pockets, one on each side of the frond midvein. The small midvein region is also the site from which the root originates and the stem arises that connects each frond to its mother frond. The meristematic pocket is protected by a tissue flap. Fronds bud alternately from these pockets. Doubling times vary by species and are as short as 20-24 hours (Landolt (1957) *Ber. Schweiz. Bot. Ges.* 67:271; Chang et al. (1977) *Bull. Inst. Chem. Acad. Sin.* 24:19; Datko and Mudd (1970) *Plant Physiol.* 65:16; Venkataraman et al. (1970) *Z. Pflanzenphysiol.* 62: 316).

Intensive culture of duckweed results in the highest rates of biomass accumulation per unit time (Landolt and Kandeler (1987) *The Family of Lemnaceae—A Monographic Study Vol. 2: Phytochemistry, Physiology, Application, Bibliography* (Veroffentlichungen des Geobotanisches Institutes ETH, Stiftung Rubel, Zurich)), with dry weight accumulation ranging from 6-15% of fresh weight (Tillberg et al. (1979) *Physiol. Plant.* 46:5; Landolt (1957) *Ber. Schweiz. Bot. Ges.* 67:271; Stomp, unpublished data). Protein content of a number of duckweed species grown under varying conditions has been reported to range from 15-45% dry weight (Chang et al. (1977) *Bull. Inst. Chem. Acad. Sin.* 24:19; Chang and Chui (1978) *Z. Pflanzenphysiol.* 89:91; Porath et al. (1979) *Aquatic Botany* 7:272; Appenroth et al. (1982) *Biochem. Physiol. Pflanz.* 177:251). Using these values, the level of protein production per liter of medium in duckweed is on the same order of magnitude as yeast gene expression systems.

Duckweed plant or duckweed nodule cultures can be efficiently transformed with an expression cassette containing a nucleotide sequence of interest by any one of a number of methods including *Agrobacterium*-mediated gene transfer, ballistic bombardment, or electroporation. Stable duckweed transformants can be isolated by transforming the duckweed cells with both the nucleotide sequence of interest and a gene that confers resistance to a selection agent, followed by culturing the transformed cells in a medium containing the selection agent. See U.S. Pat. No. 6,040,498 to Stomp et al.

A duckweed gene expression system provides the pivotal technology that would be useful for a number of research and commercial applications. For plant molecular biology research as a whole, a differentiated plant system that can be manipulated with the laboratory convenience of yeast provides a very fast system in which to analyze the developmental and physiological roles of isolated genes. For commercial production of valuable polypeptides, a duckweed-based system has a number of advantages over existing microbial or cell culture systems. Plants demonstrate post-translational processing that is similar to mammalian cells, overcoming one major problem associated with the microbial cell production of biologically active mammalian polypeptides, and it has been shown by others that plant systems have the ability to assemble multi-subunit proteins, an ability often lacking in microbial systems (Hiatt (1990) *Nature* 334:469). Scale-up of duckweed biomass to levels necessary for commercial production of recombinant proteins is faster and more cost efficient than similar scale-up of mammalian cells, and unlike other suggested plant production systems, for example, soybeans and tobacco, duckweed can be grown in fully contained and controlled biomass production vessels, making the system's integration into existing protein production industrial infrastructure far easier.

Accordingly, there remains a need for optimized compositions and methods for expressing proteins of interest in duckweed.

BRIEF SUMMARY OF THE INVENTION

Compositions and methods for regulating gene expression in a plant are provided. Compositions include novel nucleotide sequences for expression control elements (e.g., promoters and introns) isolated from *Lemnaceae* ubiquitin, replacement (r)-histone and chitinase genes. The expression control elements of the invention initiate transcription of operably linked heterologous nucleotide sequences in plants. More particularly, the compositions of the invention include the expression control elements set forth in SEQ ID NOs:1-3, 13 and 14, and variants and fragments thereof. Compositions also include novel intron sequences within these *Lemnaceae* expression control elements, particularly the intron sequences set forth in SEQ ID NOs:7-9 and variants and fragments thereof. These intron sequences can be operably linked to a promoter of interest to enhance expression of an operably linked heterologous nucleotide sequence in a plant.

Also provided is a novel *Lemnaceae* chitinase signal peptide set forth in SEQ ID NO:16, encoded by a sequence set forth in SEQ ID NO:15, and variants and fragments thereof. The signal peptide-encoding sequence can be operably linked to a coding sequence for a polypeptide of interest to direct extracellular secretion of the encoded polypeptide.

Expression constructs (e.g., cassettes and vectors) comprising an expression control element and/or intron and/or signal peptide-encoding sequence of the invention operably linked to a heterologous nucleotide sequence of interest are provided. Stably transformed plants, plant cells and nodules having an expression construct of the invention are further provided.

The compositions of the invention find use in methods directed to expressing nucleotide sequences of interest in a plant or plant cell or nodule. The methods of the invention include introducing into a plant or plant cell or nodule an expression construct having a *Lemnaceae* ubiquitin, r-histone or chitinase expression control element (e.g., as set forth in SEQ ID NOs:1-3, 13 and 14), or a variant or fragment thereof, operably linked to a nucleotide sequence of interest. The methods of the invention further comprise introducing into a plant or plant cell or nodule an expression construct including an expression control element isolated from the *Lemna gibba* ribulose-1,5-bisphosphate carboxylase small subunit gene (RbcS; e.g., as set forth in SEQ ID NOs:10-12). In other embodiments, methods of the invention include introducing into a plant or plant cell or nodule an expression construct having a *Lemnaceae* chitinase signal peptide-encoding sequence (e.g., as set forth in SEQ ID NO:15), or a variant or fragment thereof, operably linked to the coding sequence for a polypeptide of interest.

In some embodiments, the methods of the invention are directed to the production of a polypeptide encoded by a nucleotide sequence of interest in a plant expression system (e.g., a duckweed expression system). The plant expression system of the present invention is optimized to produce high levels of the polypeptide sequence of interest. Thus, the invention encompasses methods for the expression of a nucleotide sequence of interest in plants that are transformed with expression constructs for the expression of the nucleotide sequence of interest, where these nucleotide sequences are modified to enhance their expression in plants.

These and other aspects of the invention are disclosed in more detail in the description of the invention given below.

DETAILED DESCRIPTION OF THE INVENTION

The present invention provides compositions and methods directed to novel nucleic acids for plant expression control elements that regulate transcription of heterologous nucleotide sequences in plants. Specifically, the compositions of the invention comprise expression control elements isolated from the *Lemnaceae* ubiquitin, r-histone and chitinase genes, including the expression control elements set forth in SEQ ID NOs:1-3, 13 and 14, and variants and fragments thereof, as defined herein below. The individual promoter (SEQ ID NOs: 4-6, 13 and 14) and intron (SEQ ID NOs:7-9) sequences within these expression control elements also find use in regulating transcription in plants. The invention also provides a novel *L. minor* chitinase signal peptide (SEQ ID NO:16) and the corresponding coding sequence (SEQ ID NO:15), and variants and fragments thereof.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

The invention encompasses isolated or substantially purified nucleic acid compositions. An "isolated" or "purified" nucleic acid molecule is substantially or essentially free from components that normally accompany or interact with the nucleic acid molecule or protein as found in its naturally occurring environment. Thus, an isolated or purified nucleic acid molecule is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

The compositions of the invention include isolated nucleic acid molecules comprising the expression control element nucleotide sequences set forth in SEQ ID NOs:1-3, 13 and 14, and variants and fragments thereof, as defined herein below. By "expression control element" is intended a regulatory region of DNA usually comprising a TATA box capable of directing RNA polymerase II to initiate RNA synthesis at the appropriate transcription initiation site for a particular coding sequence. An expression control element may additionally comprise other recognition sequences generally positioned upstream or 5' to the TATA box, which influence (e.g., enhance) the transcription initiation rate. Furthermore, an expression control element may additionally comprise sequences generally positioned downstream or 3' to the TATA box, which influence (e.g., enhance) the transcription initiation rate.

It is recognized that having identified the nucleotide sequences for the expression control element regions disclosed herein, it is within the state of the art to isolate and identify further regulatory elements in the 5' untranslated region (UTR) upstream from the particular expression control element regions identified herein. Thus, for example, the expression control element regions disclosed herein may further comprise additional regulatory elements such as those responsible for tissue and temporal expression of the coding sequence, enhancers, and the like. See particularly Australian Patent No. AU-A-77751/94 and U.S. Pat. Nos. 5,466,785 and 5,635,618 (both of which are herein incorporated by reference).

The expression control elements of the invention were isolated from ubiquitin, r-histone and chitinase genes for several members of the *Lemnaceae* family, and are thus referred to as "*Lemnaceae* expression control elements." SEQ ID NO:1 sets forth the full-length *Lemna minor* ubiquitin expression control element, including both the promoter plus 5' UTR (nucleotides 1-1625) and intron (nucleotides 1626-2160). SEQ ID NO:2 sets forth the full-length *Spirodella polyrrhiza* ubiquitin expression control element, including both the promoter plus 5' UTR (nucleotides 1-1041) and intron (nucleotides 1042-2021). SEQ ID NO:3 sets forth the full-length *Lemna aequinoctialis* ubiquitin expression control element, including both the promoter plus 5' UTR (nucleotides 1-964) and intron (nucleotides 965-2068). SEQ ID NO:4 sets forth the promoter plus 5' UTR portion of the *L. minor* ubiquitin expression control element. SEQ ID NO:5 sets forth the promoter plus 5' UTR portion of the *S. polyrrhiza* ubiquitin expression control element. SEQ ID NO:6 sets forth the promoter plus 5'UTR portion of the *L. aequinoctialis* ubiquitin expression control element. SEQ ID NO:7 sets forth the intron portion of the *L. minor* ubiquitin expression control element. SEQ ID NO:8 sets forth the intron portion of the *S. polyrrhiza* ubiquitin expression control element. SEQ ID NO:9 sets forth the intron portion of the *L. aequinoctialis* ubiquitin expression control element.

SEQ ID NO:13 sets forth the full-length *Lemna minor* r-histone expression control element, including the promoter plus 5' UTR. SEQ ID NO:14 sets forth the full-length *Lemna minor* chitinase expression control element, including the promoter plus 5' UTR. SEQ ID NO:15 sets forth the *L. minor* chitinase signal peptide-encoding sequence. SEQ ID NO:16 sets forth the *L. minor* chitinase signal peptide.

It is recognized that the individual promoter plus 5' UTR sequences set forth in SEQ ID NOs:4-6, 13 and 14, and biologically active variants and fragments thereof, can be used to regulate transcription of operably linked nucleotide sequences of interest in plants. Similarly, one or more of the intron sequences set forth in SEQ ID NOs:7-9, and biologically active fragments or variants thereof, can be operably linked to a promoter of interest, including a promoter set forth in SEQ ID NO:4, 5, 6, 13, or 14 in order to enhance expression of a nucleotide sequence that is operably linked to that promoter.

Fragments and variants of the disclosed expression control elements, signal peptide-encoding sequence, and encoded signal peptide are also encompassed by the present invention. By "fragment" in the context of an expression control element is intended a portion of the full-length expression control element, such as a portion of any one of the expression control elements set forth in SEQ ID NOs:1-3, 13 and 14. Fragments of an expression control element retain biological activity and hence encompass fragments capable of initiating or enhancing expression of an operably linked nucleotide sequence. Thus, for example, less than the entire expression control elements disclosed herein may be utilized to drive expression of an operably linked nucleotide sequence of interest, such as a nucleotide sequence encoding a heterologous protein. Specific, non-limiting examples of such fragments of an expression control element include: (i) the nucleotide sequences set forth in any one of SEQ ID NOs:4-9 (as described herein above); (ii) 5' truncations of the *L. minor* ubiquitin expression control element (SEQ ID NO:1), such as nucleotides 1288-2160 of SEQ ID NO:1 (LmUbq truncated promoter No. 1, as found in the Egs22 construct described herein below) and nucleotides 1132-2160 of SEQ ID NO:1 (LmUbq truncated promoter No. 2, as found in the Egs23 construct described herein below); (iii) 5' truncations of the *L. minor* r-histone expression control element (SEQ ID NO:13), such as nucleotides 461-1808 of SEQ ID NO:13 (LmHIS (461-1808), as found in the Egs19 construct described herein below) and nucleotides 805-1808 of SEQ ID NO:13 (LmHIS (805-1808), as found in the Egs20 construct described herein below); and (iv) 5' truncations of the *L. minor* chitinase expression control element (SEQ ID NO:14), such as nucleotides 51-1338 of SEQ ID NO:14 (LmCHT (51-1338), as found in the Egs24 and Egs25 constructs described herein below).

As used herein, "full-length sequence" in reference to a specified nucleotide sequence means having the entire nucleic acid sequence of a native sequence. By "native sequence" is intended an endogenous sequence, that is, a non-engineered sequence found in an organism's genome.

Thus, a fragment of a *Lemnaceae* expression control element can function as a biologically active portion of the expression control element. A biologically active portion of a expression control element can be prepared by isolating a portion of one of the expression control elements of the invention and assessing the activity (e.g., the ability to initiate or enhance transcription) of that portion of the expression control element. Nucleic acid molecules that are fragments of an expression control element comprise at least 15, 20, 25, 30, 35, 40, 45, 50, 75, 100, 325, 350, 375, 400, 425, 450, 500, 550, 600, 650, 700, 800, 900, 1200, 1500, 1800, or 2000 contiguous nucleotides, or up to the number of nucleotides present in the full-length expression control elements disclosed herein (i.e., 2160 nucleotides for SEQ ID NO: 1, 2021 nucleotides for SEQ ID NO:2, 2068 nucleotides for SEQ ID NO:3, 1808 nucleotides for SEQ ID NO:13, and 1338 nucleotides for SEQ ID NO:14).

The nucleotides of such fragments will usually comprise the TATA recognition sequence of the particular expression control element. Such fragments can be obtained by use of restriction enzymes to cleave the naturally occurring expression control elements disclosed herein; by synthesizing a nucleotide sequence from the naturally occurring sequence of the expression control element DNA sequence; or can be obtained through the use of polymerase chain reaction (PCR) technology. See particularly, Mullis et al. (1987) *Methods Enzymol.* 155:335-350, and Erlich, ed. (1989) *PCR Technology* (Stockton Press, New York). Variants of these expression control element fragments, such as those resulting from site-directed mutagenesis, are also encompassed by the compositions of the present invention.

"Fragment" in the context of a signal peptide-encoding sequence and encoded signal peptide is intended to mean a portion of the coding sequence or a portion of the signal peptide encoded thereby. With respect to coding sequences, fragments of a nucleotide sequence can encode polypeptide fragments that retain the biological activity of the native polypeptide, in this case, the native *L. minor* chitinase signal peptide. Thus, a functional fragment of the *L. minor* chitinase signal peptide directs movement of a mature protein of interest through the secretory pathway of a plant cell. Fragments of a coding nucleotide sequence can range from at least about 20 nucleotides, about 25 nucleotides, about 50 nucleotides, about 75 nucleotides, and up to the entire nucleotide sequence encoding the *L. minor* chitinase signal peptide (i.e., up to 84 nucleotides of SEQ ID NO:15).

By "variants" is intended sequences having substantial similarity with an expression control element disclosed herein (e.g., SEQ ID NOs:1-3, 13 and 14) or a fragment thereof (e.g., the sequences set forth in SEQ ID NOs:4-9), or with a signal peptide-encoding sequence (e.g., SEQ ID NO:15) or a signal peptide (e.g., SEQ ID NO:16) or a fragment thereof. For nucleotide sequences, naturally occurring variants such as these can be identified with the use of well-known molecular biology techniques, as, for example, with PCR and hybridization techniques as outlined below. Variant nucleotide sequences also include synthetically derived nucleotide sequences, such as those generated, for example, by using site-directed mutagenesis. Generally, variants of a particular nucleotide sequence of the invention, including variants of any of SEQ ID NOs:1-9 and 13-15, will have at least 40%, 50%, 60%, 65%, 70%, generally at least 75%, 80%, 85%, preferably about 90%, 91%, 92%, 93%, 94%, to 95%, 96%, 97%, and more preferably about 98%, 99% or more sequence identity to that particular nucleotide sequence as determined by sequence alignment programs described herein below using default parameters. Biologically active variants are also encompassed by the present invention. Biologically active variants include, for example, the native expression control elements, or native signal peptide-encoding sequence, of the invention having one or more nucleotide substitutions, deletions, or insertions.

As used herein, "sequence identity" or "identity" in the context of two nucleic acid sequences or two polypeptide sequences makes reference to the residues in the two sequences that are the same when aligned for maximum correspondence over a specified comparison window. By "comparison window" is intended a contiguous and specified segment of a polynucleotide/polypeptide sequence, where the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids in length, and optionally can be 30, 40, 50, 100 nucleotides/amino acids, or longer.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters.

The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) *CABIOS* 4:11-17. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) *Proc. Natl. Acad. Sci. USA* 87:2264. BLAST nucleotide searches can be performed with the BLASTN program, score=100, word length=12, to obtain nucleotide sequences homologous to a nucleotide sequence of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) *Nucleic Acids Res.* 25:3389. When utilizing BLAST, Gapped BLAST, PSI-BLAST, the default parameters of the respective programs (e.g., BLASTN for nucleotide sequences and BLASTX for proteins) can be used.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1992) *Proc. Natl. Acad. Sci. USA* 89: 10915). Alignment may also be performed manually by inspection.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found, for example, in Sambrook et al. (2001) *Molecular Cloning: A Laboratory Manual* (Cold Spring Harbor Laboratory Press, Cold Spring Harbor, N.Y.) and Tijssen (1993) *Hybridization With Nucleic Acid Probes, Part I: Theory and*

*Nucleic Acid Preparation* (Laboratory Techniques in Biochemistry and Molecular Biology, Elsevier Science Ltd., NY, N.Y.).

For purposes of the present invention, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

Expression control element activity for any of the *Lemnaceae* expression control elements, or fragments or variants thereof, can be assayed using a variety of techniques well known to one of ordinary skill in the art, including, for example, Northern blot analysis, reporter activity measurements taken from transcriptional fusions, and the like. See, for example, Sambrook et al. (2001) *Molecular Cloning: A Laboratory Manual* (Cold Spring Harbor Laboratory Press, Cold Spring Harbor, N.Y.). Alternatively, expression control element assays may be based on the measurement of levels of a reporter gene such as β-glucuronidase (GUS), green fluorescent protein (GFP), or the like produced under the control of an expression control element, or fragment or variant thereof. See, for example, U.S. Pat. No. 6,072,050, herein incorporated by reference. Activity of the *L. minor* chitinase signal peptide, or fragments or variants thereof, can likewise by assayed using a variety of techniques well known to one of ordinary skill in the art, including those that detect the ability of the chitinase signal peptide, or fragment or variant thereof, to direct extracellular secretion of a polypeptide of interest.

Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192 (herein incorporated by reference); Walker and Gaastra, eds. (1983) *Techniques in Molecular Biology* (MacMillan Publishing Company, NY) and the references cited therein.

The *Lemnaceae* expression control elements of the present invention, and variants or fragments thereof, when assembled within a nucleotide construct such that the expression control element is operably linked to a nucleotide sequence of interest, enable expression of the operably linked nucleotide sequence in a plant or plant cell or nodule (e.g., a duckweed plant or duckweed plant cell or nodule, such as from the genus *Spirodela*, genus *Wolffia*, genus *Wolfiella*, genus *Landoltia*, or genus *Lemna*). By "operably linked" is intended that the transcription or translation of the nucleotide sequence of interest is under the influence of the expression control element. In this manner, the nucleotide sequences for the expression control elements of the invention are provided in expression cassettes or vectors along with the nucleotide sequence of interest, typically a heterologous nucleotide sequence, for expression in the plant or plant cell or nodule. By "heterologous nucleotide sequence" is intended a sequence that is not naturally operably linked with the expression control element. While this nucleotide sequence is heterologous to the expression control element, it may be homologous, or native, or heterologous, or foreign, to the plant host.

It is recognized that the expression control elements of the invention, or variants or fragments thereof, can be used to drive expression of the respective native coding sequence. Such constructs can change expression levels of the native polypeptide in the plant or plant cell. Thus, the phenotype of the plant or plant cell can be altered.

As used herein, "vector" refers to a DNA molecule such as a plasmid, cosmid, or bacterial phage for introducing a nucleotide construct, for example, an expression cassette, into a host cell. Cloning vectors typically contain one or a small number of restriction endonuclease recognition sites at which foreign DNA sequences can be inserted in a determinable fashion without loss of essential biological function of the vector, as well as a marker gene, as described herein below, that is suitable for use in the identification and selection of cells transformed with the cloning vector.

As used herein, the term "plant" includes reference to whole plants, plant organs (e.g., leaves, stems, roots, etc.), seeds, plant cells, and progeny of same. Parts of transgenic plants are to be understood within the scope of the invention to comprise, for example, plant cells, protoplasts, tissues, callus, embryos as well as flowers, ovules, stems, fruits, leaves, roots, root tips, and the like originating in transgenic plants or their progeny previously transformed with a DNA molecule of the invention and therefore consisting at least in part of transgenic cells. As used herein, the term "plant cell" includes, without limitation, cells of seeds, embryos, meristematic regions, callus tissue, leaves, roots, shoots, gametophytes, sporophytes, pollen, and microspores. The class of plants that can be used in the methods of the invention is generally as broad as the class of higher plants amenable to transformation techniques, including both monocotyledonous and dicotyledonous plants. Such plants include, for example, duckweed.

The term "duckweed" refers to members of the family *Lemnaceae*. This family currently is divided into five genera and 38 species of duckweed as follows: genus *Lemna* (*L. aequinoctialis, L. disperma, L. ecuadoriensis, L. gibba, L. japonica, L. minor, L. miniscula, L. obscura, L. perpusilla, L. tenera, L. trisulca, L. turionifera, L. valdiviana*); genus *Spirodela* (*S. intermedia, S. polyrrhiza, S. punctata*); genus *Wolffia* (*Wa. angusta, Wa. arrhiza, Wa. australina, Wa. borealis, Wa. brasiliensis, Wa. columbiana, Wa. elongata, Wa. globosa, Wa. microscopica, Wa. neglecta*); genus *Wolfiella* (*Wl. caudata, Wl. denticulata, Wl. gladiata, Wl. hyalina, Wl. lingulata, Wl. repunda, Wl. rotunda*, and *Wl. neotropica*) and genus *Landoltia* (*L. punctata*). Any other genera or species of *Lemnaceae*, if they exist, are also aspects of the present invention. *Lemna* species can be classified using the taxonomic scheme described by Landolt (1986) *Biosystematic Investigation on the Family of Duckweeds: The family of Lemnaceae—A Monograph Study* (Geobatanischen Institut ETH, Stiftung Rubel, Zurich).

The term "duckweed nodule" as used herein refers to duckweed tissue comprising duckweed cells where at least about 50%, 55%, 60%, 65%, 70%, 75%, 80%, 85%, 90%, 95%, or 100% of the cells are differentiated cells. A "differentiated cell," as used herein, is a cell with at least one phenotypic characteristic (e.g., a distinctive cell morphology or the expression of a marker nucleic acid or protein) that distinguishes it from undifferentiated cells or from cells found in other tissue types. The differentiated cells of the duckweed nodule culture described herein form a tiled smooth surface of interconnected cells fused at their adjacent cell walls, with nodules that have begun to organize into frond primordium scattered throughout the tissue. The surface of the tissue of the nodule culture has epidermal cells connected to each other via plasmadesmata.

In some embodiments, expression cassettes or vectors comprising a *Lemnaceae* expression control element, or a variant or fragment thereof, operably linked to a nucleotide sequence of interest are provided for expression of the polypeptide encoded by the nucleotide sequence of interest in a plant or plant cell or nodule. The operably linked nucleotide sequence of interest may be any sequence whose expression in a plant or plant cell or nodule is desirable. The nucleotide sequence of interest will typically be a heterologous nucleotide sequence, as defined herein. Exemplary heterologous nucleotide sequences of interest include, but are not limited to, sequences that encode mammalian polypeptides, such as insulin, growth hormone, α-interferon, β-interferon, β-glucocerebrosidase, β-glucoronidase, retinoblastoma protein, p53 protein, angiostatin, leptin, erythropoietin, granulocyte macrophage colony stimulating factor, plasminogen, monoclonal antibodies, Fab fragments, single chain antibodies, cytokines, receptors, human vaccines, animal vaccines, peptides, and serum albumin.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

In a specific, non-limiting example, transformed duckweed is obtained by transformation with an expression cassette comprising a *Lemnaceae* ubiquitin expression control element (e.g., as set forth in SEQ ID NOs:1-3), a fragment thereof (e.g., as set forth in SEQ ID NOs:4-9), a *Lemnaceae* r-histone expression control element (e.g., as set forth in SEQ ID NO:13), a *Lemnaceae* chitinase expression control element (e.g., as set forth in SEQ ID NO:14), or a variant of these sequences operably linked to a heterologous nucleotide sequence of interest. Transformed duckweed can also be obtained by transformation with an expression cassette comprising a *Lemna gibba* RbcS expression control element (e.g., as set forth in SEQ ID NOs:10-12; see GenBank Accession Nos. S45165 (SSU13; nucleotides 694-757), S45166 (SSU5A; nucleotides 698-755) and S45167 (SSU5B; nucleotides 690-751)), or a variant or fragment thereof, operably linked to a heterologous nucleotide sequence of interest. The expression control elements set forth in SEQ ID NOs:10-12 advantageously enhance expression of operably linked heterologous nucleotide sequences in transformed duckweed compared to expression without the elements.

An expression cassette of the invention is provided with a plurality of restriction sites for insertion of the nucleotide sequence encoding the protein of interest to be under the transcriptional regulation of the expression control element. The expression cassette may encode a single gene of interest. Alternatively, the expression cassette may encode two or more genes of interest.

The expression cassettes described herein include in the 5'-3' direction of transcription, a transcriptional and translational initiation region (e.g., an expression control element of the invention or biologically active variant or fragment thereof), a nucleotide sequence of interest, and a transcriptional and translational termination region functional in plants. Any suitable termination sequence known in the art may be used in accordance with the present invention. The termination region may be native with the transcriptional initiation region, may be native with the nucleotide sequence of interest, or may be derived from another source. Convenient termination regions are available from the Ti-plasmid of *A. tumefaciens*, such as the octopine synthetase and nopaline synthetase termination regions. See also Guerineau et al. (1991) *Mol. Gen. Genet.* 262:141; Proudfoot (1991) *Cell* 64:671; Sanfacon et al. (1991) *Genes Dev.* 5:141; Mogen et al. (1990) *Plant Cell* 2:1261; Munroe et al. (1990) *Gene* 91:151; Ballas et al. (1989) *Nucleic Acids Res.* 17:7891; and Joshi et al. (1987) *Nucleic Acids Res.* 15:9627. Additional exemplary termination sequences are the pea RubP carboxylase small subunit termination sequence, the Cauliflower Mosaic Virus 35S termination sequence, and the ubiquitin terminator from many plant species. Other suitable termination sequences will be apparent to those skilled in the art.

Generally, the expression cassette will comprise a selectable marker gene for the selection of transformed cells or tissues. Selectable marker genes include genes encoding antibiotic resistance, such as those encoding neomycin phosphotransferase II (NEO), neomycin phosphotransferase III and hygromycin phosphotransferase (HPT), as well as genes conferring resistance to herbicidal compounds. Herbicide resistance genes generally code for a modified target protein insensitive to the herbicide or for an enzyme that degrades or detoxifies the herbicide in the plant before it can act. See, DeBlock et al. (1987) *EMBO J.* 6:2513; DeBlock et al. (1989) *Plant Physiol.* 91:691; Fromm et al. (1990) *BioTechnology* 8:833; Gordon-Kamm et al. (1990) *Plant Cell* 2:603; and Frisch et al. (1995) *Plant Mol. Biol.* 27:405-9. For example, resistance to glyphosate or sulfonylurea herbicides has been obtained using genes coding for the mutant target enzymes, 5-enolpyruvylshikimate-3-phosphate synthase (EPSPS) and acetolactate synthase (ALS). Resistance to glufosinate ammonium, boromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides.

For purposes of the present invention, selectable marker genes include, but are not limited to, genes encoding neomycin phosphotransferase II (Fraley et al. (1986) *CRC Critical Reviews in Plant Science* 4:1), neomycin phosphotransferase III (Frisch et al. (1995) *Plant Mol. Biol.* 27:405-9), cyanamide hydratase (Maier-Greiner et al. (1991) *Proc. Natl. Acad. Sci. USA* 88:4250); aspartate kinase; dihydrodipicolinate synthase (Perl et al. (1993) *BioTechnology* 11:715); bar gene (Toki et al. (1992) *Plant Physiol.* 100: 1503; Meagher et al. (1996) *Crop Sci.* 36:1367); tryptophan decarboxylase (Goddijn et al. (1993) *Plant Mol. Biol.* 22:907); neomycin phosphotransferase (NEO; Southern et al. (1982) *J. Mol. Appl. Gen.* 1:327); hygromycin phosphotransferase (HPT or HYG; Shimizu et al. (1986) *Mol. Cell. Biol.* 6:1074); dihydrofolate reductase (DHFR; Kwok et al. (1986) *Proc. Natl. Acad. Sci. USA* 83:4552); phosphinothricin acetyltransferase (DeBlock et al. (1987) *EMBO J.* 6:2513); 2,2-dichloropropionic acid dehalogenase (Buchanan-Wollatron et al. (1989) *J. Cell. Biochem.* 13D:330); acetohydroxyacid synthase (U.S. Pat. No. 4,761,373 to Anderson et al.; Haughn et al. (1988) *Mol. Gen. Genet.* 221:266); 5-enolpyruvyl-shikimate-phosphate synthase (aroA; Comai et al. (1985) *Nature* 317:741); haloarylnitrilase (WO 87/04181 to Stalker et al.); acetyl-coenzyme A carboxylase (Parker et al. (1990) *Plant Physiol.* 92:1220); dihydropteroate synthase (sulI; Guerineau et al. (1990) *Plant Mol. Biol.* 15:127); and 32 kDa photosystem II polypeptide (psbA; Hirschberg et al. (1983) *Science* 222:1346 (1983).

Also included are genes encoding resistance to gentamicin (e.g., aacC1, Wohlleben et al. (1989) *Mol. Gen. Genet.* 217: 202-208); chloramphenicol (Herrera-Estrella et al. (1983) *EMBO J.* 2:987); methotrexate (Herrera-Estrella et al. (1983) *Nature* 303:209; Meijer et al. (1991) *Plant Mol. Biol.* 16:807); hygromycin (Waldron et al. (1985) *Plant Mol. Biol.* 5:103; Zhijian et al. (1995) *Plant Science* 108:219; Meijer et al. (1991) *Plant Mol. Bio.* 16:807); streptomycin (Jones et al. (1987) *Mol. Gen. Genet.* 210:86); spectinomycin (Bretagne-Sagnard et al. (1996) *Transgenic Res.* 5:131); bleomycin (Hille et al. (1986) *Plant Mol. Biol.* 7:171); sulfonamide (Guerineau et al. (1990) *Plant Mol. Bio.* 15:127); bromoxynil (Stalker et al. (1988) *Science* 242:419); 2,4-D (Streber et al. (1989) *BioTechnology* 7:811); phosphinothricin (DeBlock et al. (1987) *EMBO J.* 6:2513); spectinomycin (Bretagne-Sagnard and Chupeau, *Transgenic Research* 5:131).

The bar gene confers herbicide resistance to glufosinate-type herbicides, such as phosphinothricin (PPT) or bialaphos, and the like. Other selectable markers that could be used in the expression constructs include, but are not limited to, the PAT gene, also for bialaphos and phosphinothricin resistance, the ALS gene for imidazolinone resistance, the HPH or HYG gene for hygromycin resistance, the EPSP synthase gene for glyphosate resistance, the Hm1 gene for resistance to the Hc-toxin, and other selective agents used routinely and known to one of ordinary skill in the art. See Yarranton (1992) *Curr. Opin. Biotech.* 3:506; Chistopherson et al. (1992) *Proc. Natl. Acad. Sci. USA* 89:6314; Yao et al. (1992) *Cell* 71:63; Reznikoff (1992) *Mol. Microbiol.* 6:2419; Barkley et al. (1980) *The Operon* 177-220; Hu et al. (1987) *Cell* 48:555; Brown et al. (1987) *Cell* 49:603; Figge et al. (1988) *Cell* 52:713; Deuschle et al. (1989) *Proc. Natl. Acad. Sci. USA* 86:5400; Fuerst et al. (1989) *Proc. Natl. Acad. Sci. USA* 86:2549; Deuschle et al. (1990) *Science* 248:480; Labow et al. (1990) *Mol. Cell. Biol.* 10:3343; Zambretti et al. (1992) *Proc. Natl. Acad. Sci. USA* 89:3952; Baim et al. (1991) *Proc. Natl. Acad. Sci. USA* 88:5072; Wyborski et al. (1991) *Nuc. Acids Res.* 19:4647; Hillenand-Wissman (1989) *Topics in Mol. And Struc. Biol.* 10:143; Degenkolb et al. (1991) *Antimicrob. Agents Chemother.* 35:1591; Kleinschnidt et al. (1988) *Biochemistry* 27:1094; Gatz et al. (1992) *Plant J.* 2:397; Gossen et al. (1992) *Proc. Natl. Acad. Sci. USA* 89:5547; Oliva et al. (1992) *Antimicrob. Agents Chemother.* 36:913; Hlavka et al. (1985) *Handbook of Experimental Pharmacology* 78; and Gill et al. (1988) *Nature* 334:721. Such disclosures are herein incorporated by reference.

The above list of selectable marker genes are not meant to be limiting. Any lethal or non-lethal selectable marker gene can be used in the present invention.

In some embodiments, the present invention provides for the modification of the expressed nucleotide sequence of interest to enhance its expression in the plant of interest. Methods are available in the art for synthesizing nucleotide sequences with plant-preferred codons. See, for example, U.S. Pat. Nos. 5,380,831 and 5,436,391 (both of which are herein incorporated by reference); Perlak et al. (1991) *Proc. Natl. Acad. Sci. USA* 15:3324; Tannacome et al. (1997) *Plant Mol. Biol.* 34:485; and Murray et al. (1989) *Nucleic Acids. Res.* 17:477.

For example, where the plant of interest is duckweed, one such modification is the synthesis of the nucleotide sequence of interest using duckweed-preferred codons. The preferred codons may be determined from the codons of highest frequency in the proteins expressed in duckweed. Thus, the frequency of usage of particular a codon in duckweed may be determined by analyzing codon usage in a group of duckweed coding sequences. A number of duckweed coding sequences are known to those of skill in the art; see for example, the sequences contained in the GenBank® database, which may be accessed through the website for the National Center for Biotechnology Information, a division of the National Library of Medicine, which is located in Bethesda, Md. Tables showing the frequency of codon usage based on the sequences contained in the most recent GenBank® release may be found on the website for the Kazusa DNA Research Institute in Chiba, Japan. This database is described in Nakamura et al. (2000) *Nucleic Acids Res.* 28:292.

It is recognized that genes that have been optimized for expression in duckweed and other monocots or dicots can be used in the methods of the invention. See, e.g., EP 0 359 472, EP 0 385 962, WO 91/16432; Perlak et al. (1991) *Proc. Natl. Acad. Sci. USA* 88:3324; Iannacome et al. (1997) *Plant Mol. Biol.* 34:485; Murray et al. (1989) *Nucleic Acids Res.* 17:477; and the like. It is further recognized that all or any part of the gene sequence may be optimized or synthetic. In other words, fully optimized or partially optimized sequences may also be used. For example, 40%, 45%, 50%, 55%, 60%, 65%, 70%, 75%, 80%, 85%, 87%, 90%, 91%, 92%, 93%, 94%, 95%, 96%, 97%, 98%, 99%, or 100% of the codons may be plant-preferred codons, for example, duckweed-preferred codons. Thus, in some embodiments, the nucleotide sequence encoding the polypeptide of interest comprises between 50-100% duckweed-preferred codons or between 70-100% duckweed-preferred codons. In one embodiment, between 90 and 96% of the codons are duckweed-preferred codons. The coding sequence of the nucleotide sequence of interest may comprise codons used with a frequency of at least 17% in duckweed. Codon usage in *Lemna gibba* (Table 1) and *Lemna minor* (Table 2) is shown below. In some embodiments, Table 1 or Table 2 is used to select duckweed-preferred codons.

TABLE 1

*Lemna gibba* codon usage from GenBank ® Release 139*

| Amino Acid | Codon | Number | /1000 | Fraction |
|---|---|---|---|---|
| Gly | GGG | 57.00 | 28.89 | 0.35 |
| Gly | GGA | 8.00 | 4.05 | 0.05 |
| Gly | GGT | 3.00 | 1.52 | 0.02 |
| Gly | GGC | 93.00 | 47.14 | 0.58 |
| Glu | GAG | 123.00 | 62.34 | 0.95 |
| Glu | GAA | 6.00 | 3.04 | 0.05 |
| Asp | GAT | 6.00 | 3.04 | 0.08 |
| Asp | GAC | 72.00 | 36.49 | 0.92 |
| Val | GTG | 62.00 | 31.42 | 0.47 |
| Val | GTA | 0.00 | 0.00 | 0.00 |
| Val | GTT | 18.00 | 9.12 | 0.14 |
| Val | GTC | 51.00 | 25.85 | 0.39 |
| Ala | GCG | 44.00 | 22.30 | 0.21 |
| Ala | GCA | 14.00 | 7.10 | 0.07 |
| Ala | GCT | 14.00 | 7.10 | 0.07 |
| Ala | GCC | 139.00 | 70.45 | 0.66 |
| Arg | AGG | 16.00 | 8.11 | 0.15 |
| Arg | AGA | 11.00 | 5.58 | 0.10 |
| Ser | AGT | 1.00 | 0.51 | 0.01 |
| Ser | AGC | 44.00 | 22.30 | 0.31 |
| Lys | AAG | 116.00 | 58.79 | 1.00 |
| Lys | AAA | 0.00 | 0.00 | 0.00 |
| Asn | AAT | 2.00 | 1.01 | 0.03 |
| Asn | AAC | 70.00 | 35.48 | 0.97 |
| Met | ATG | 67.00 | 33.96 | 1.00 |
| Ile | ATA | 4.00 | 2.03 | 0.06 |
| Ile | ATT | 0.00 | 0.00 | 0.00 |

TABLE 1-continued

*Lemna gibba* codon usage from GenBank ® Release 139*

| Amino Acid | Codon | Number | /1000 | Fraction |
|---|---|---|---|---|
| Ile | ATC | 63.00 | 31.93 | 0.94 |
| Thr | ACG | 19.00 | 9.63 | 0.25 |
| Thr | ACA | 1.00 | 0.51 | 0.01 |
| Thr | ACT | 6.00 | 3.04 | 0.08 |
| Thr | ACC | 50.00 | 25.34 | 0.66 |
| Trp | TGG | 45.00 | 22.81 | 1.00 |
| End | TGA | 4.00 | 2.03 | 0.36 |
| Cys | TGT | 0.00 | 0.00 | 0.00 |
| Cys | TGC | 34.00 | 17.23 | 1.00 |
| End | TAG | 0.00 | 0.00 | 0.00 |
| End | TAA | 7.00 | 3.55 | 0.64 |
| Tyr | TAT | 4.00 | 2.03 | 0.05 |
| Tyr | TAC | 76.00 | 38.52 | 0.95 |
| Leu | TTG | 5.00 | 2.53 | 0.04 |
| Leu | TTA | 0.00 | 0.00 | 0.00 |
| Phe | TTT | 4.00 | 2.03 | 0.04 |
| Phe | TTC | 92.00 | 46.63 | 0.96 |
| Ser | TCG | 34.00 | 17.23 | 0.24 |
| Ser | TCA | 2.00 | 1.01 | 0.01 |
| Ser | TCT | 1.00 | 0.51 | 0.01 |
| Ser | TCC | 59.00 | 29.90 | 0.42 |
| Arg | CGG | 23.00 | 11.66 | 0.22 |
| Arg | CGA | 3.00 | 1.52 | 0.03 |
| Arg | CGT | 2.00 | 1.01 | 0.02 |
| Arg | CGC | 50.00 | 25.34 | 0.48 |
| Gln | CAG | 59.00 | 29.90 | 0.86 |
| Gln | CAA | 10.00 | 5.07 | 0.14 |
| His | CAT | 5.00 | 2.53 | 0.26 |
| His | CAC | 14.00 | 7.10 | 0.74 |
| Leu | CTG | 43.00 | 21.79 | 0.35 |
| Leu | CTA | 2.00 | 1.01 | 0.02 |
| Leu | CTT | 1.00 | 0.51 | 0.01 |
| Leu | CTC | 71.00 | 35.99 | 0.58 |
| Pro | CCG | 44.00 | 22.30 | 0.31 |
| Pro | CCA | 6.00 | 3.04 | 0.04 |
| Pro | CCT | 13.00 | 6.59 | 0.09 |
| Pro | CCC | 80.00 | 40.55 | 0.56 |

TABLE 2

*Lemna minor* codon usage from GenBank ® Release 139*

| AmAcid | Codon | Number | /1000 | Fraction |
|---|---|---|---|---|
| Gly | GGG | 8.00 | 17.39 | 0.22 |
| Gly | GGA | 11.00 | 23.91 | 0.31 |
| Gly | GGT | 1.00 | 2.17 | 0.03 |
| Gly | GGC | 16.00 | 34.78 | 0.44 |
| Glu | GAG | 25.00 | 54.35 | 0.78 |
| Glu | GAA | 7.00 | 15.22 | 0.22 |
| Asp | GAT | 8.00 | 17.39 | 0.33 |
| Asp | GAC | 16.00 | 34.78 | 0.67 |
| Val | GTG | 21.00 | 45.65 | 0.53 |
| Val | GTA | 3.00 | 6.52 | 0.07 |
| Val | GTT | 6.00 | 13.04 | 0.15 |
| Val | GTC | 10.00 | 21.74 | 0.25 |
| Ala | GCG | 13.00 | 28.26 | 0.32 |
| Ala | GCA | 8.00 | 17.39 | 0.20 |
| Ala | GCT | 6.00 | 13.04 | 0.15 |
| Ala | GCC | 14.00 | 30.43 | 0.34 |
| Arg | AGG | 9.00 | 19.57 | 0.24 |
| Arg | AGA | 11.00 | 23.91 | 0.30 |
| Ser | AGT | 2.00 | 4.35 | 0.05 |
| Ser | AGC | 11.00 | 23.91 | 0.26 |
| Lys | AAG | 13.00 | 28.26 | 0.68 |
| Lys | AAA | 6.00 | 13.04 | 0.32 |
| Asn | AAT | 0.00 | 0.00 | 0.00 |
| Asn | AAC | 12.00 | 26.09 | 1.00 |
| Met | ATG | 9.00 | 19.57 | 1.00 |
| Ile | ATA | 1.00 | 2.17 | 0.08 |
| Ile | ATT | 2.00 | 4.35 | 0.15 |
| Ile | ATC | 10.00 | 21.74 | 0.77 |
| Thr | ACG | 5.00 | 10.87 | 0.28 |

TABLE 2-continued

*Lemna minor* codon usage from GenBank ® Release 139*

| AmAcid | Codon | Number | /1000 | Fraction |
|---|---|---|---|---|
| Thr | ACA | 2.00 | 4.35 | 0.11 |
| Thr | ACT | 2.00 | 4.35 | 0.11 |
| Thr | ACC | 9.00 | 19.57 | 0.50 |
| Trp | TGG | 8.00 | 17.39 | 1.00 |
| End | TGA | 1.00 | 2.17 | 1.00 |
| Cys | TGT | 1.00 | 2.17 | 0.12 |
| Cys | TGC | 7.00 | 15.22 | 0.88 |
| End | TAG | 0.00 | 0.00 | 0.00 |
| End | TAA | 0.00 | 0.00 | 0.00 |
| Tyr | TAT | 1.00 | 2.17 | 0.12 |
| Tyr | TAC | 7.00 | 15.22 | 0.88 |
| Leu | TTG | 3.00 | 6.52 | 0.08 |
| Leu | TTA | 1.00 | 2.17 | 0.03 |
| Phe | TTT | 6.00 | 13.04 | 0.25 |
| Phe | TTC | 18.00 | 39.13 | 0.75 |
| Ser | TCG | 11.00 | 23.91 | 0.26 |
| Ser | TCA | 4.00 | 8.70 | 0.09 |
| Ser | TCT | 6.00 | 13.04 | 0.14 |
| Ser | TCC | 9.00 | 19.57 | 0.21 |
| Arg | CGG | 4.00 | 8.70 | 0.11 |
| Arg | CGA | 4.00 | 8.70 | 0.11 |
| Arg | CGT | 0.00 | 0.00 | 0.00 |
| Arg | CGC | 9.00 | 19.57 | 0.24 |
| Gln | CAG | 11.00 | 23.91 | 0.73 |
| Gln | CAA | 4.00 | 8.70 | 0.27 |
| His | CAT | 0.00 | 0.00 | 0.00 |
| His | CAC | 6.00 | 13.04 | 1.00 |
| Leu | CTG | 9.00 | 19.57 | 0.24 |
| Leu | CTA | 4.00 | 8.70 | 0.11 |
| Leu | CTT | 4.00 | 8.70 | 0.11 |
| Leu | CTC | 17.00 | 36.96 | 0.45 |
| Pro | CCG | 8.00 | 17.39 | 0.29 |
| Pro | CCA | 7.00 | 15.22 | 0.25 |
| Pro | CCT | 5.00 | 10.87 | 0.18 |
| Pro | CCC | 8.00 | 17.39 | 0.29 |

Other modifications can also be made to the nucleotide sequence of interest to optimize its expression in a plant. These modifications include, but are not limited to, elimination of sequences encoding spurious polyadenylation signals, exon-intron splice site signals, transposon-like repeats, and other such well characterized sequences that may be deleterious to gene expression. The G-C content of the sequence may be adjusted to levels average for a given cellular host, as calculated by reference to known genes expressed in the host cell. When possible, the sequence may be modified to avoid predicted hairpin secondary mRNA structures.

There are known differences between the optimal translation initiation context nucleotide sequences for translation initiation codons in animals and plants and the composition of these translation initiation context nucleotide sequences can influence the efficiency of translation initiation. See, for example, Lukaszewicz et al. (2000) *Plant Science* 154:89-98; and Joshi et al. (1997) *Plant Mol. Biol.* 35:993-1001. In some embodiments of the present invention, the translation initiation context nucleotide sequence for the translation initiation codon of the nucleotide sequence of interest may be modified to enhance expression in duckweed. In one embodiment, the nucleotide sequence is modified such that the three nucleotides directly upstream of the translation initiation codon of the nucleotide sequence of interest are "ACC." In a second embodiment, these nucleotides are "ACA."

In addition to the expression control elements described herein for initiating or enhancing expression of a heterologous nucleotide sequence in a plant, expression of a nucleotide sequence of interest can also be enhanced by the optional use of various regulatory elements. "Regulatory element" as used herein, refers to a nucleotide sequence, either DNA or RNA, usually upstream (5') of the coding sequence of a structural gene, including transcriptional control sequences such as leader sequences, promoters, translational and transcriptional enhancers or repressors, and mRNA stability and instability determinants. Sequences found within introns may also regulate expression of the coding region of interest. Regulatory elements can also be found 3' to the site of transcription initiation, or within transcribed regions. The various regulatory elements can be operably linked to other regulatory elements. "Leader sequence" as used herein refers to the portion of a nucleic acid located at the 5' end of mRNA, extending from the 5'CAP site to the AUG protein translation initiation codon. The leader sequence is important in translation initiation and in gene expression regulation.

For example, one or more leader sequences may additionally be used in combination to enhance expression of the target nucleotide sequence. Translation leaders are known in the art and include, but are not limited to, picornavirus leaders, e.g., EMCV leader (Encephalomyocarditis 5' noncoding region; Elroy-Stein et al. (1989) *Proc. Natl. Acad. Sci. USA* 86:6126); potyvirus leaders, e.g., TEV leader (Tobacco Etch Virus; Gallie et al. (1995) *Gene* 165:233); human immunoglobulin heavy-chain binding protein (BiP; Macajak and Sarnow (1991) *Nature* 353:90); untranslated leader from the coat protein mRNA of alfalfa mosaic virus (AMV RNA 4; Jobling and Gehrke (1987) *Nature* 325:622); tobacco mosaic virus leader (TMV; Gallie (1989) *Molecular Biology of RNA*, 23:56); potato etch virus leader (Tomashevskaya et al. (1993) *J. Gen. Virol.* 74:2717-2724); Fed-1 5' untranslated region (Dickey (1992) *EMBO J.* 11:2311-2317); RbcS 5' untranslated region (Silverthorne et al. (1990) *J. Plant. Mol. Biol.* 15:49-58); and maize chlorotic mottle virus leader (MCMV; Lommel et al. (1991) *Virology* 81:382). See also, Della-Cioppa et al. (1987) *Plant Physiology* 84:965. Leader sequences comprising a plant intron sequence, including the intron sequence from the maize dehydrogenase 1 gene, the castor bean catalase gene, or the *Arabidopsis* tryptophan pathway gene PAT1, have also been shown to increase translational efficiency in plants (Callis et al. (1987) *Genes Dev.* 1:1183-1200; Mascarenhas et al. (1990) *Plant Mol. Biol.* 15:913-920).

The *Lemnaceae* ubiquitin introns described herein above (i.e., as set forth in SEQ ID NOs:7-9) can be used with promoters other than their respective ubiquitin promoters to enhance expression of an operably linked nucleotide sequence of interest. The promoter used with the ubiquitin introns can be any promoter suitable for use in the plant of interest, including the novel *Lemnaceae* r-histone and chitinase promoters disclosed in SEQ ID NOs:13 and 14, respectively. Other suitable promoters can be obtained from a variety of sources, such as plants or plant DNA viruses. Useful promoters include those isolated from the caulimovirus group, such as the cauliflower mosaic virus 19S and 35S (CaMV19S and CaMV35S) transcript promoters. Other useful promoters include the enhanced CaMV35S promoter (eCaMV35S) as described by Kat et al. (1987) Science 236: 1299-1302, and the small subunit promoter of ribulose 1,5-bisphosphate carboxylase oxygenase (RUBISCO). Examples of other suitable promoters are rice actin promoter; cyclophilin promoter; ADH1 promoter (Callis et al. (1987) *Gene Dev.* 1:1183-1200); Class I patatin promoter (Bevan et al. (1986) *Nucl. Acids Res.* 14:4675-4638); ADP glucose pyrophosphorylase promoter; β-conglycinin promoter (Tiemey et al. (1987) *Planta* 172:356-363); E8 promoter (Deikman et al. (1988) *Embo J.* 7:3315-3320); 2AII promoter (Pear et al. (1989) *Plant Mol. Biol.* 13:639-651); and acid chitinase promoter (Samac et al. (1990) *Plant Physiol.* 93:907-914).

It is recognized that any of the expression-enhancing nucleotide sequence modifications described above can be used in the present invention, including any single modification or any possible combination of modifications.

In some embodiments, the compositions and methods of the invention are utilized in a plant expression system, for example, a duckweed expression system, and the heterologous nucleotide sequence of interest is a secreted protein. Secreted proteins are usually translated from precursor polypeptides that include a "signal peptide" that interacts with a receptor protein on the membrane of the endoplasmic reticulum (ER) to direct the translocation of the growing polypeptide chain across the membrane and into the endoplasmic reticulum for secretion from the cell. This signal peptide is often cleaved from the precursor polypeptide to produce a "mature" polypeptide lacking the signal peptide. In this manner, a biologically active polypeptide is expressed in a plant, for example, duckweed, from an expression construct having an expression control element of the invention, or a biologically active variant or fragment thereof, operably linked to a nucleotide sequence of interest that is further operably linked with a nucleotide sequence encoding a signal peptide that directs secretion of the polypeptide into the culture medium. A "biologically active polypeptide" refers to a polypeptide that has the capability of performing one or more biological functions or a set of activities normally attributed to the polypeptide in a biological context. Plant signal peptides that target protein translocation to the endoplasmic reticulum (for secretion outside of the cell) are known in the art. See, for example, U.S. Pat. No. 6,020,169, herein incorporated by reference.

In one embodiment, the signal peptide is the novel *L. minor* chitinase signal peptide set forth in SEQ ID NO:16, or a variant or fragment thereof, and the expression construct includes a nucleotide sequence encoding this signal peptide operably linked to a nucleotide sequence of interest. In some embodiments, this signal peptide-encoding sequence is the sequence set forth in SEQ ID NO:15.

It is recognized that the *L. minor* chitinase signal peptide of the invention, or variants or fragments thereof, can be used to direct extracellular secretion of any encoded polypeptide of interest. In this manner, the signal peptide-encoding sequence of SEQ ID NO:15, or a variant or fragment thereof, can be incorporated into any expression construct such that it is operably linked in proper reading frame to a promoter of interest and a polypeptide-encoding nucleotide sequence of interest. Such an expression construct can be introduced into a plant or plant cell or nodule to provide for expression and extracellular secretion of the encoded polypeptide of interest.

Alternatively, a mammalian signal peptide can be used to target recombinant polypeptides expressed in genetically engineered plants, for example, duckweed, for secretion. It has been demonstrated that plant cells recognize mammalian signal peptides that target the endoplasmic reticulum, and that these signal peptides can direct the secretion of polypeptides not only through the plasma membrane but also through the plant cell wall. See, for example, U.S. Pat. Nos. 5,202,422 and 5,639,947, both of which are incorporated herein by reference.

The secreted polypeptide can be harvested from the culture medium by any conventional means known in the art and purified by chromatography, electrophoresis, dialysis, solvent-solvent extraction, and the like.

The methods of the invention involve introducing an expression construct into a plant or plant cell or nodule. By "introducing" is intended presenting to the plant an expression construct in such a manner that the construct gains access to the interior of a cell of the plant. The methods of the invention do not depend on a particular method for introducing an expression construct to a plant, only that the expression construct gains access to the interior of at least one cell of the plant. Methods for introducing expression constructs into plants are known in the art including, but not limited to, stable transformation methods, transient transformation methods, and virus-mediated methods.

By "stable transformation" is intended that a nucleotide sequence introduced into a plant integrates into the genome of the plant and is capable of being inherited by progeny thereof. By "transient transformation" is intended that a nucleotide sequence (e.g., a nucleotide sequence contained in an expression construct) introduced into a plant does not integrate into the genome of the plant.

The nucleotide sequences of the invention may be introduced into plants or plant cells or nodules by contacting the plants or plant cells or nodules with a virus or viral nucleic acids. Generally, such methods involve incorporating a nucleotide sequence of the invention within a viral DNA or RNA molecule. Methods for introducing nucleotide sequences into plants or plant cells or nodules and expressing a protein encoded therein, involving viral DNA or RNA molecules, are known in the art. See, for example, U.S. Pat. Nos. 5,889,191, 5,889,190, 5,866,785, 5,589,367, and 5,316,931, each of which is herein incorporated by reference.

Transformation protocols as well as protocols for introducing nucleotide sequences into plants may vary depending on the type of plant or plant cell or nodule, that is, monocot or dicot, targeted for transformation. Suitable methods of introducing nucleotide sequences into plants or plant cells or nodules include microinjection (Crossway et al. (1986) *Biotechniques* 4:320-334), electroporation (Riggs et al. (1986) *Proc. Natl. Acad. Sci. USA* 83:5602-5606), *Agrobacterium*-mediated transformation (U.S. Pat. Nos. 5,563,055 and 5,981,840, both of which are herein incorporated by reference), direct gene transfer (Paszkowski et al. (1984) *EMBO J.* 3:2717-2722), and ballistic particle acceleration (see, e.g., U.S. Pat. Nos. 4,945,050; 5,879,918; 5,886,244; and 5,932,782 (each of which is herein incorporated by reference); and Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926). The cells that have been transformed may be grown into plants in accordance with conventional ways. See, for example, McCormick et al. (1986) *Plant Cell Reports* 5:81-84.

In some embodiments, the stably transformed duckweed plants or duckweed plant cells or nodules express biologically active polypeptides that cannot effectively be commercially produced by existing gene expression systems, because of cost or logistical constraints, or both. For example, some proteins cannot be expressed in mammalian systems because the protein interferes with cell viability, cell proliferation, cellular differentiation, or protein assembly in mammalian cells. Such proteins include, but are not limited to, retinoblastoma protein, p53, angiostatin, and leptin. The present invention can be advantageously employed to produce mammalian regulatory proteins; it is unlikely given the large evolutionary distance between higher plants and mammals that these proteins will interfere with regulatory processes in duckweed. Transgenic duckweed can also be used to produce large quantities of proteins such as serum albumin (in particular, human serum albumin), hemoglobin, and collagen, which challenge the production capabilities of existing expression systems.

Additionally, higher plant systems can be engineered to produce biologically active multimeric proteins (e.g., monoclonal antibodies, hemoglobin, P450 oxidase, and collagen, and the like) far more easily than can mammalian systems. One exemplary approach for producing biologically active multimeric proteins in duckweed uses an expression construct containing the genes encoding all of the polypeptide subunits. See, e.g., During et al. (1990) *Plant Mol. Biol.* 15:281 and van Engelen et al. (1994) *Plant Mol. Biol.* 26:1701. This construct is then introduced into duckweed cells using any known transformation method, such as a ballistic bombardment or *Agrobacterium*-mediated transformation. This method results in clonal cell lines that express all of the polypeptides necessary to assemble the multimeric protein. A variation on this approach is to make single gene constructs, mix DNA from these constructs together, then deliver this mixture of DNAs into plant cells using ballistic bombardment or *Agrobacterium*-mediated transformation. As a further variation, some or all of the constructs may encode more than one subunit of the multimeric protein (i.e., so that there are fewer duckweed clones to be crossed than the number of subunits in the multimeric protein). Alternatively, each duckweed clone expresses at least one of the subunits of the multimeric protein, and duckweed clones secreting each subunit are cultured together and the multimeric protein is assembled in the media from the various secreted subunits. In some instances, it may be desirable to produce less than all of the subunits of a multimeric protein, or even a single protein subunit, in a transformed duckweed plant or duckweed nodule culture, for example, for industrial or chemical processes or for diagnostic, therapeutic, or vaccination purposes.

The following examples are offered for purposes of illustration, not by way of limitation.

EXPERIMENTAL

Example 1

Expression Vectors

The expression vectors used in the examples described below include Egs05, Egs07, Egs11, Egs22, Egs23, Egs46, Egs50, Egs51, Egs19, Egs20, Egs24, Egs25, IFN53, and IFN54. Egs05 and Egs07 are unmodified expression vectors comprising a control promoter operably linked to the coding sequence for *E. coli* β-glucuronidase (GUS), each with a different selectable marker gene. Egs11 comprises the full-length *L. minor* ubiquitin expression control element (SEQ ID NO:1) operably linked to the GUS coding sequence, with a selectable marker gene. Egs22 and Egs23 are similar constructs, but use truncated versions of the *L. minor* ubiquitin expression control element. In Egs22, nucleotides 1288-2160 of SEQ ID NO:1 drive expression of the operably linked GUS coding sequence. In Egs23, nucleotides 1132-2160 of SEQ ID NO:1 drive expression of this GUS coding sequence. Egs46 is similar to Egs11, but comprises a different selectable marker gene.

Egs50 comprises the full-length *S. polyrrhiza* ubiquitin expression control element (SEQ ID NO:2) operably linked to the GUS coding sequence, with a selectable marker gene. Similarly, Egs51 comprises the full-length *L. aequinoctialis* ubiquitin expression control element (SEQ ID NO:3) operably linked to the GUS coding sequence, with a selectable marker gene.

Egs19 comprises nucleotides 461-1808 of the *L. minor* r-histone expression control element (SEQ ID NO:13) operably linked to the GUS coding sequence, with a selectable marker gene. In Egs20, nucleotides 805-1808 of SEQ ID NO:13 drive expression of the GUS coding sequence.

Egs24 comprises nucleotides 51-1338 of the *L. minor* chitinase expression control element (SEQ ID NO:14) operably linked to the GUS coding sequence, with a selectable marker gene. Egs25 comprises nucleotides 51-1338 of the *L. minor* chitinase expression control element (SEQ ID NO:14) operably linked to the maize ADH1 intron and GUS coding sequence, with a selectable marker gene.

The IFN53 and IFN54 expression vectors each contain the AmasPmas super promoter, *L. gibba* RbcS SSU5B expression control element (SEQ ID NO:12), and maize ADH1 intron operably linked to a codon-optimized interferon alpha-2b gene, with either a codon-optimized alpha amylase signal sequence (IFN53) or the *L. minor* chitinase signal sequence (SEQ ID NO:15; IFN54).

Example 2

Transformation of Duckweed

Duckweed fronds or duckweed nodule cultures (derived from *Lemna minor* strain 8627 in these examples) were transformed with the expression constructs described above using *Agrobacterium*-mediated transformation methods. *Agrobacterium tumefaciens* strain C58Z707, a disarmed, broad host range C58 strain (Hepburn et al. (1985) *J. Gen. Microbiol.* 131:2961-2969) is used for transformation in these examples. The expression constructs described above were mobilized into *A. tumefaciens* by electroporation, or by a triparental mating procedure using *E. coli* MM294 harboring the mobilizing plasmid pRK2013 (Hoekema et al. (1983) *Nature* 303: 179-180; Ditta et al. (1980) *Proc. Natl. Acad. Sci. USA* 77:7347-7350). C58Z707 strains comprising the expression constructs described above are streaked on AB minimal medium (Chilton et al. (1974) *Proc. Nat. Acad. Sci. USA* 71:3672-3676) or in YEB or LB medium (1 g/L yeast extract, 5 g/L beef extract, 5 g/L peptone, 5 g/L sucrose, 0.5 g/L $MgSO_4$) containing streptomycin at 500 mg/L, spectinomycin at 50 mg/L and kanamycin sulfate at 50 mg/L and grown overnight at 28° C.

Duckweed nodule cultures for transformation were produced as follows. Duckweed fronds were separated, the roots are cut off with a sterile scalpel, and the fronds are placed, ventral side down, on Murashige and Skoog medium (catalog number M-5519; Sigma Chemical Corporation, St. Louis, Mo.) pH 5.6, supplemented with 5 µM 2,4-dichlorophenoxyacetic acid, 0.5 µM 1-Phenyl-3(1,2,3-thiadiazol-5-yl) urea thidiazuron (Sigma P6186), 3% sucrose, 0.4 Difco Bacto-agar (Fisher Scientific), and 0.15% Gelrite (Sigma). Fronds were grown for 5-6 weeks. At this time, the nodules (small, yellowish cell masses) appeared, generally from the central part of the ventral side. This nodule tissue was detached from the mother frond and cultured in Murashige and Skoog medium supplemented with 3% sucrose, 0.4% Difco Bacto-agar, 0.15% Gelrite, 1 µM 2,4-dichlorophenoxyacetic acid, and 2 µM benzyladenine.

Duckweed nodule cultures were transformed as follows. The appropriate *Agrobacterium tumefaciens* strain was grown on potato dextrose agar or YEB or LB agar with 50 mg/L kanamycin and 100 µM acetosyringone, and resuspended in Murashige and Skoog medium supplemented with 0.6 M Mannitol and 100 µM acetosyringone. Nodule culture tissue was inoculated by immersing in the solution of resuspended bacteria for 1-2 minutes, blotted to remove excess fluid, and plated on co-cultivation medium consisting of Murashige and Skoog medium supplemented with auxin and cytokinin optimized to promote nodule growth and 100 µM acetosyringone. See, Yamamoto et al. (2001) *In Vitro Cell Dev. Biol. Plant* 37:349-353.

For selection, nodule culture tissue was transferred to regeneration medium; 0.5× Schenk and Hildebrandt medium supplemented with 1% sucrose 0.4% Difco Bacto-Agar, 0.15% Gelrite 500 mg/L cefotaxime, and 6 mg/L geneticin and cultured for approximately 6-8 weeks under continuous light (20-40 µM/m²·sec). The nodule tissue was transferred every 7 days to fresh culture medium. Selection is complete when the nodule tissue shows vigorous growth on the selection agent.

Example 3

Transient Expression of *E. coli* GUS in Duckweed

Transient GUS expression was assessed in duckweed nodule cultures transformed with the Egs05, Egs07, Egs11, Egs22, Egs23, Egs46, Egs50, Egs51, Egs19, Egs20, Egs24, and Egs25 constructs. All constructs were capable of driving strong expression of GUS, as determined by 24 hour staining (Table 3).

Additionally, GUS enzyme assays were carried out on duckweed nodule cultures transformed with the Egs07, Egs46, Egs50, and Egs51 constructs. The 36 Egs07 transgenic lines averaged 1.345% GUS, the 29 Egs46 transgenic lines averaged 2.320% GUS, the 4 Egs50 transgenic lines averaged 4.008% GUS, and the 8 Egs51 transgenic lines averaged 6.682% GUS.

TABLE 3

Transient GUS Expression in Callus

| Test Vector | Promoter | Staining |
|---|---|---|
| Egs05 | control | ++++ |
| Egs07 | control | ++++ |
| Egs11 | LmUBQ | ++++ |
| Egs22 | LmUBQ (trunc #1) | +++ |
| Egs23 | LmUBQ (trunc #2) | ++++ |
| Egs46 | LmUBQ | ++++ |
| Egs50 | SpUBQ | ++++ |
| Egs51 | LaUBQ | +++ |
| Egs19 | LmHIS (461-1808) | ++ |
| Egs20 | LmHIS (805-1808) | + |
| Egs24 | LmCHT (51-1338) | + |
| Egs25 | LmCHT (51-1338) + ADH1 intron | ++ |

24 hour staining; rated on a scale of 1 to 4.

Example 4

Expression of Interferon in Duckweed

Several hundred transgenic duckweed lines were produced using the IFN53 and IFN54 constructs and subsequently screened for interferon expression by ELISA. Similar levels of interferon expression were observed for the two constructs. IFN53: top expresser, 1735.66 ng/ml; mean expression, 362.04 ng/ml. IFN54: top expresser, 1173.81 ng/ml; mean expression, 347.40 ng/ml.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule comprising a nucleotide sequence selected from the group consisting of:
   a) a nucleotide sequence comprising the sequence set forth in SEQ ID NO: 2;
   b) a nucleotide sequence comprising at least 350 contiguous nucleotides of the sequence set forth in SEQ ID NO: 2 or 5, wherein said nucleotide sequence initiates transcription in a plant cell, and wherein the nucleotide sequence comprises a TATA box; and
   c) a nucleotide sequence comprising a functional fragment having at least 15 contiguous nucleotides of the sequence set forth in SEQ ID NO: 2 or 5, wherein said fragment initiates transcription in a plant cell.

2. An expression construct comprising the nucleic acid molecule of claim 1.

3. The expression construct of claim 2, further comprising an operably linked heterologous nucleotide sequence of interest.

4. The expression construct of claim 3, further comprising an operably linked coding sequence for a signal peptide that directs secretion of a polypeptide encoded by said heterologous nucleotide sequence of interest into culture medium.

5. The expression construct of claim 4, wherein said signal peptide comprises an amino acid sequence selected from the group consisting of:
   a) the sequence set forth in SEQ ID NO:16;
   b) a sequence having at least 95% sequence identity to the sequence set forth in SEQ ID NO:16, wherein said sequence directs secretion of said polypeptide into culture medium; and
   c) a functional fragment of the sequence set forth in SEQ ID NO:16, wherein said fragment directs secretion of said polypeptide into culture medium.

6. The expression construct of claim 5, wherein said coding sequence for said signal peptide comprises a nucleotide sequence selected from the group consisting of:
   a) the sequence set forth in SEQ ID NO:15;
   b) a sequence having at least 95% sequence identity to the sequence set forth in SEQ ID NO:15; and
   c) a fragment of the sequence set forth in SEQ ID NO:15.

7. The expression construct of claim 3, wherein said heterologous nucleotide sequence of interest encodes a mammalian polypeptide.

8. The expression construct of claim 7, wherein said mammalian polypeptide is selected from the group consisting of insulin, growth hormone, α-interferon, β-interferon, β-glucocerebrosidase, β-glucoronidase, retinoblastoma protein, p53 protein, angiostatin, leptin, erythropoietin, granulocyte macrophage colony stimulating factor, plasminogen, monoclonal antibodies, Fab fragments, single chain antibodies, cytokines, receptors, human vaccines, animal vaccines, peptides, serum albumin, and combinations thereof.

9. A plant or plant cell or nodule transformed with the expression construct of claim 2.

10. The transformed plant or plant cell or nodule of claim 9, wherein said plant or plant cell or nodule is a monocot.

11. The transformed plant or plant cell or nodule of claim 10, wherein said monocot is from a genus selected from the group consisting of the genus *Spirodela*, genus *Wolffia*, genus *Wolfiella*, genus *Landoltia*, and genus *Lemna*.

12. The transformed plant or plant cell or nodule of claim 10, wherein said monocot is a member of a species selected from the group consisting of *Lemna minor, Lemna miniscula, Lemna aequinoctialis*, and *Lemna gibba*.

13. The transformed plant or plant cell or nodule of claim 9, wherein said plant or plant cell or nodule is a dicot.

14. An isolated nucleic acid molecule comprising a nucleotide sequence selected from the group consisting of:
   a) a nucleotide sequence comprising the sequence set forth in SEQ ID NO:8; and
   b) a nucleotide sequence comprising a functional fragment of the sequence set forth in SEQ ID NO: 8, wherein said fragment enhances transcription in a plant cell.

15. An expression construct comprising the nucleic acid molecule of claim 14.

16. The expression construct of claim 15, further comprising an operably linked promoter of interest.

17. The expression construct of claim 16, wherein said promoter of interest comprises the nucleotide sequence set forth in SEQ ID NO:5.

18. A method for expressing a nucleotide sequence in a plant or plant cell or nodule, said method comprising introducing into the plant or plant cell or nodule an expression construct, said expression construct comprising an expression control element operably linked to a heterologous nucleotide sequence of interest, wherein said expression control element comprises a nucleotide sequence selected from the group consisting of:
   a) a nucleotide sequence comprising the sequence set forth in SEQ ID NO: 2;
   b) a nucleotide sequence comprising at least 350 contiguous nucleotides of the sequence set forth in SEQ ID NO: 2 or 5, wherein said nucleotide sequence initiates transcription in a plant cell, and wherein the nucleotide sequence comprises a TATA box; and
   c) a nucleotide sequence comprising a functional fragment having at least 15 contiguous nucleotides of the sequence set forth in SEQ ID NO: 2 or 5, wherein said fragment initiates transcription in a plant cell.

19. The method of claim 18, wherein said expression construct further comprises an operably linked coding sequence for a signal peptide that directs secretion of a polypeptide encoded by said heterologous nucleotide sequence of interest into culture medium.

20. The method of claim 18, wherein said heterologous nucleotide sequence of interest encodes a mammalian polypeptide.

21. The method of claim 18, wherein said heterologous nucleotide sequence of interest comprises plant-preferred codons in the coding sequence for said heterologous nucleotide sequence of interest.

22. The expression construct of claim 5, wherein said heterologous nucleotide sequence of interest encodes a mammalian polypeptide.

23. The expression construct of claim 22, wherein said mammalian polypeptide is selected from the group consisting of insulin, growth hormone, α-interferon, β-interferon, β-glucocerebrosidase, β-glucoronidase, retinoblastoma protein, p53 protein, angiostatin, leptin, erythropoietin, granulocyte macrophage colony stimulating factor, plasminogen, monoclonal antibodies, Fab fragments, single chain antibodies, cytokines, receptors, human vaccines, animal vaccines, peptides, serum albumin, and combinations thereof.

* * * * *

UNITED STATES PATENT AND TRADEMARK OFFICE
CERTIFICATE OF CORRECTION

| | | |
|---|---|---|
| PATENT NO. | : 8,034,916 B2 | Page 1 of 1 |
| APPLICATION NO. | : 12/581752 | |
| DATED | : October 11, 2011 | |
| INVENTOR(S) | : Dickey et al. | |

It is certified that error appears in the above-identified patent and that said Letters Patent is hereby corrected as shown below:

Col. 13, line 62, "Tannacome et al." should be --Iannacome et al.";

Col. 17, line 31, "Silverthome" should be --Silverthorne--;

Col. 39, Claim 1, line 55, "SEQ ID NO:2" should be --SEQ ID NO:2 or 5--;

Col. 42, Claim 18, line 14, "SEQ ID NO:2 or 5" should be --SEQ ID NO:2--; and

Col. 42, Claim 18, line 19, "SEQ ID NO: 2 or 5" should be --SEQ ID NO:2--.

Signed and Sealed this
Sixth Day of December, 2011

David J. Kappos
*Director of the United States Patent and Trademark Office*